(12) United States Patent
Blatter

(10) Patent No.: US 8,828,042 B2
(45) Date of Patent: Sep. 9, 2014

(54) BLOOD FILTER RETRIEVAL DEVICES AND METHODS

(76) Inventor: Duane D. Blatter, Salt Lake City, UT (US)

( * ) Notice: Subject to any disclaimer, the term of this patent is extended or adjusted under 35 U.S.C. 154(b) by 179 days.

(21) Appl. No.: 13/148,001

(22) PCT Filed: Feb. 4, 2010

(86) PCT No.: PCT/US2010/023245
§ 371 (c)(1),
(2), (4) Date: Aug. 4, 2011

(87) PCT Pub. No.: WO2010/091212
PCT Pub. Date: Aug. 12, 2010

(65) Prior Publication Data
US 2011/0295306 A1    Dec. 1, 2011

Related U.S. Application Data

(60) Provisional application No. 61/150,002, filed on Feb. 4, 2009.

(51) Int. Cl.
*A61M 29/00* (2006.01)
(52) U.S. Cl.
USPC .......................................................... 606/200
(58) Field of Classification Search
CPC ..... A61F 2/95; A61F 2002/011; A61F 2/966; A61F 2002/9528
USPC ............... 606/108, 191, 192, 194, 198, 200; 623/1.11, 1.12
See application file for complete search history.

(56) References Cited

U.S. PATENT DOCUMENTS

| | | | |
|---|---|---|---|
| 5,695,519 A * | 12/1997 | Summers et al. ............. | 606/200 |
| 5,824,055 A * | 10/1998 | Spiridigliozzi et al. ..... | 623/1.11 |
| 7,323,003 B2 | 1/2008 | Lowe | |
| 2002/0055747 A1* | 5/2002 | Cano et al. .................... | 606/108 |
| 2003/0093106 A1 | 5/2003 | Brady et al. | |
| 2006/0265002 A1 | 11/2006 | Huter et al. | |
| 2007/0293887 A1 | 12/2007 | Okushi et al. | |
| 2008/0125626 A1 | 5/2008 | Chang et al. | |
| 2008/0215084 A1 | 9/2008 | Boyle et al. | |

OTHER PUBLICATIONS

International Search Report dated Apr. 8, 2010, for International App. No. PCT/US2010/023245 (3 pgs.).
Written Opinion of the International Searching Authority dated Apr. 8, 2010, for International App. No. PCT/US2010/023245 (6 pgs.).
International Preliminary Report on Patentability dated Aug. 9, 2011, for International App. No. PCT/US2010/023245 (7 pgs.).

* cited by examiner

*Primary Examiner* — Jonathan W Miles
(74) *Attorney, Agent, or Firm* — Stoel Rives LLP

(57) ABSTRACT

Devices for retrieving intravascular blood filters can include sheaths into which the devices can be received. Some devices can include catches by which the filters can be manipulated to facilitate introduction of the filters into the sheaths. Some devices can include tapered regions that can align the sheaths with other portions of the devices.

65 Claims, 14 Drawing Sheets

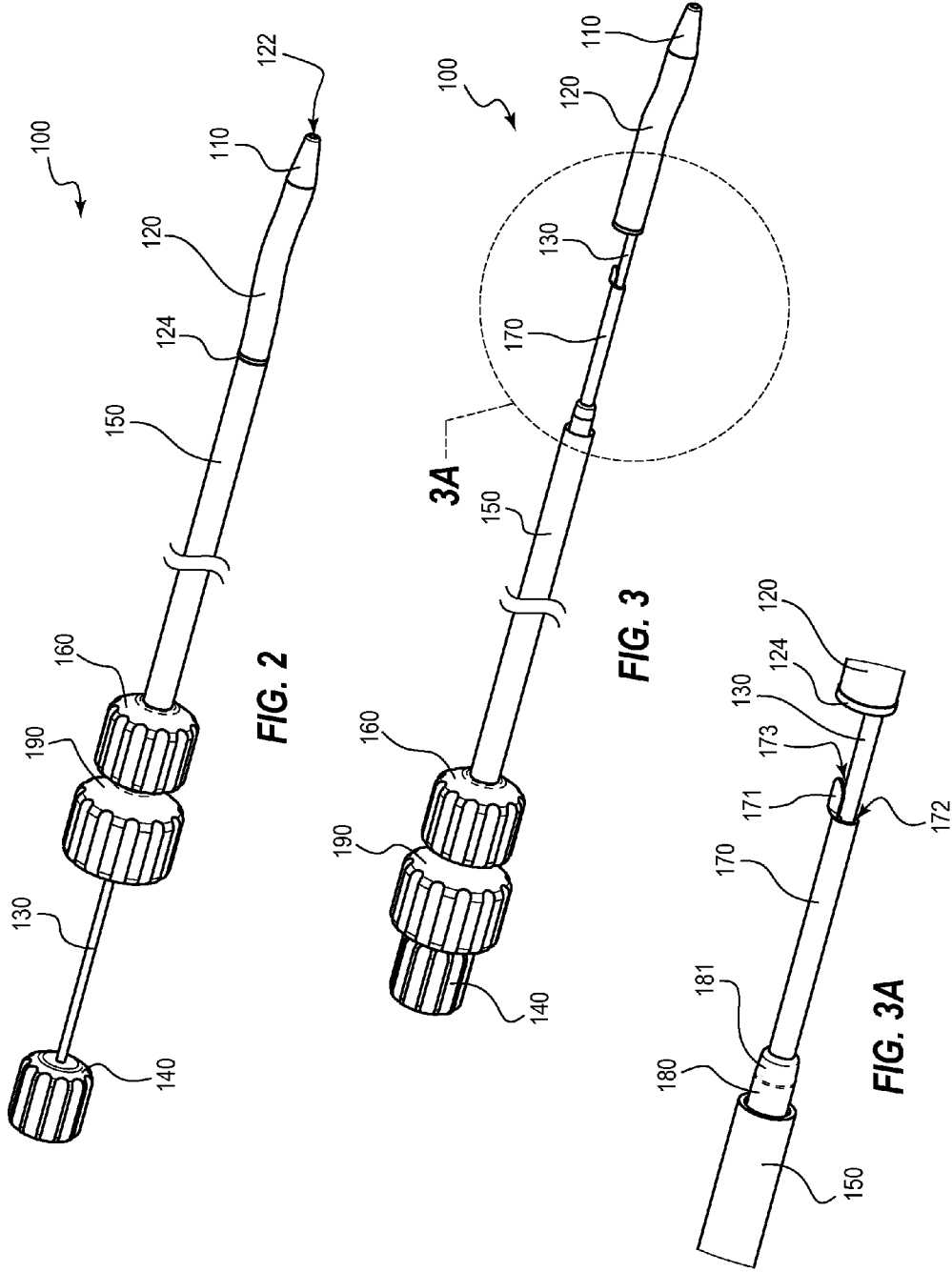

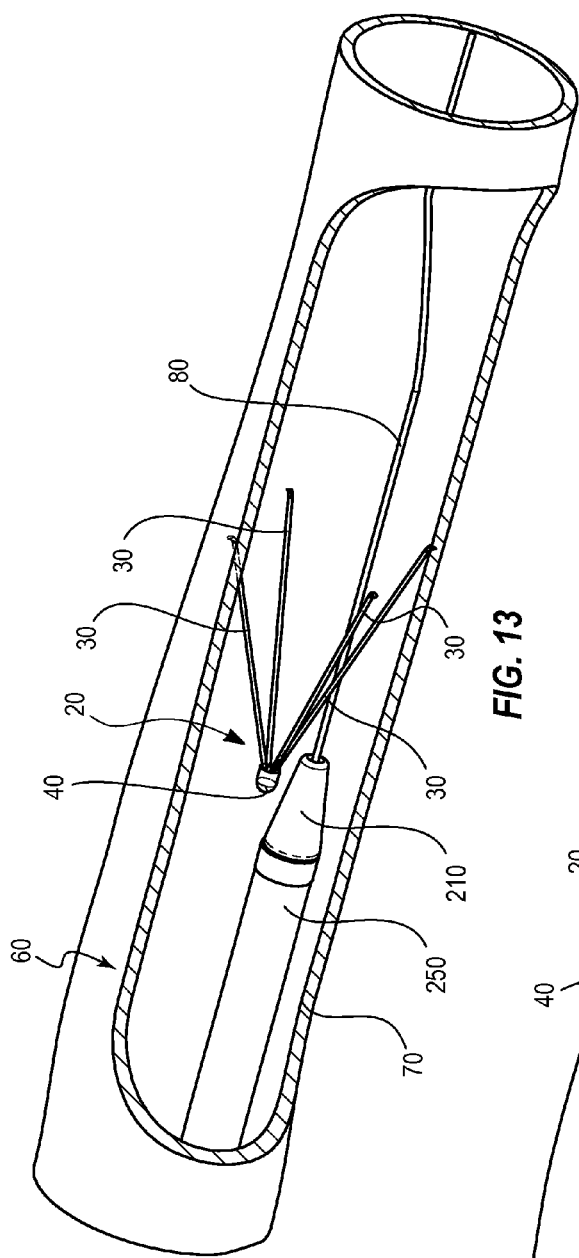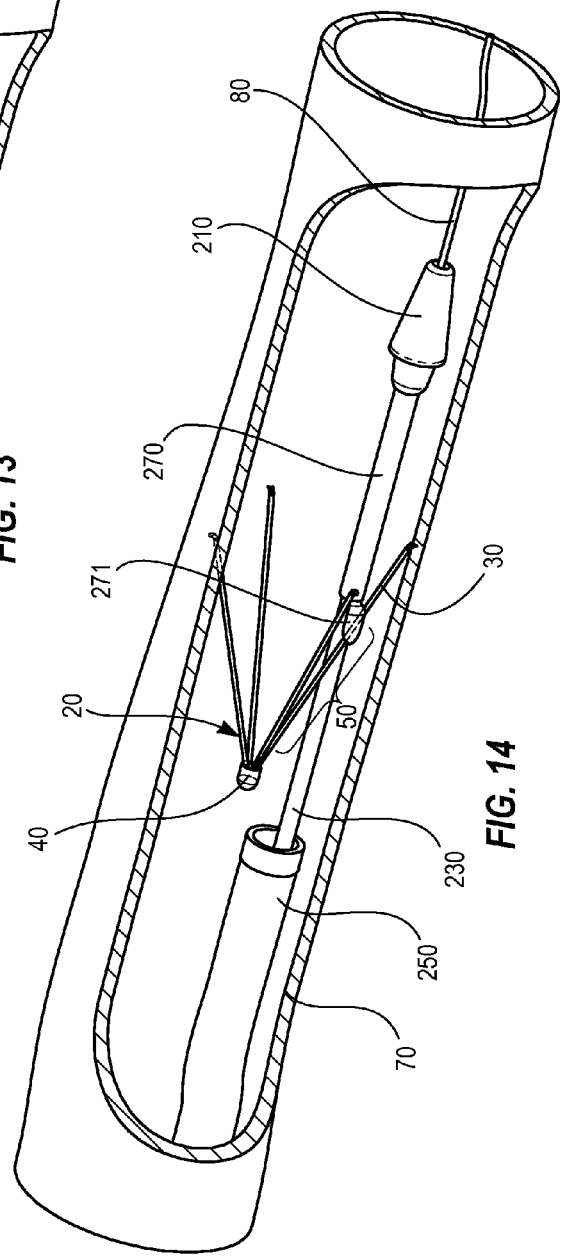

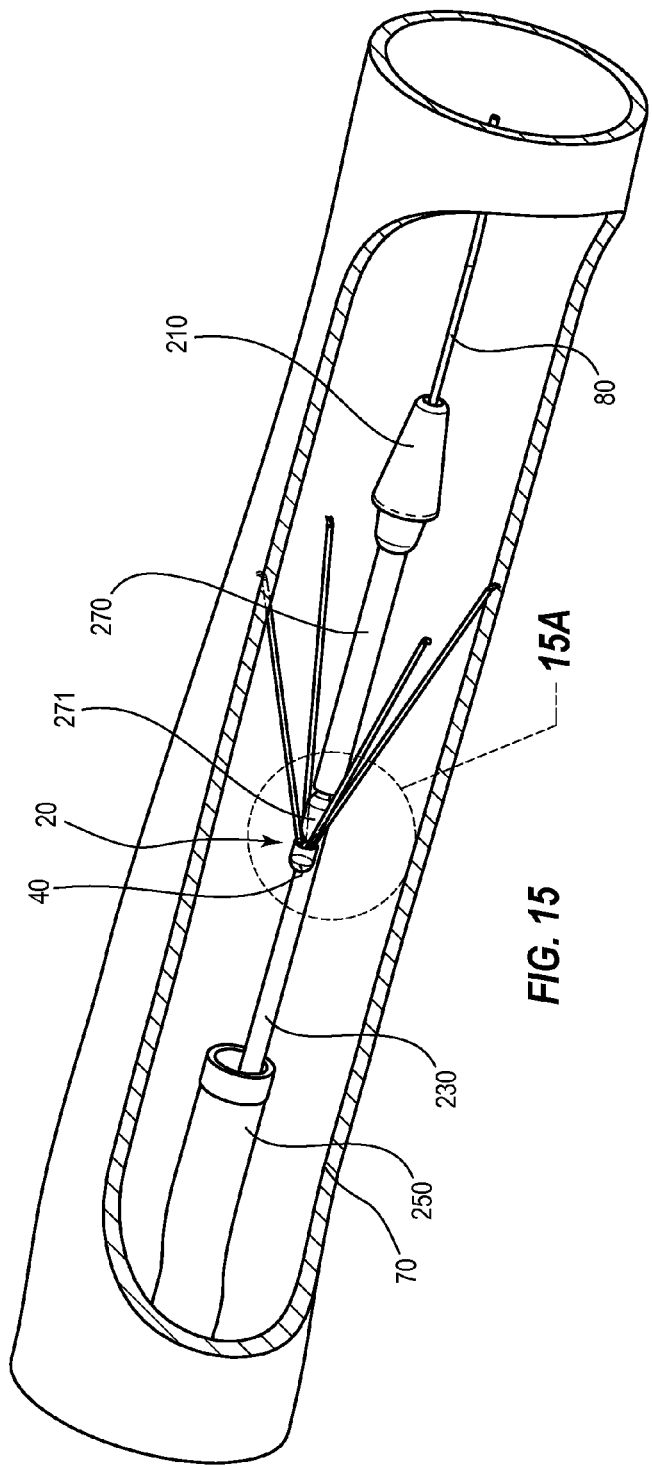
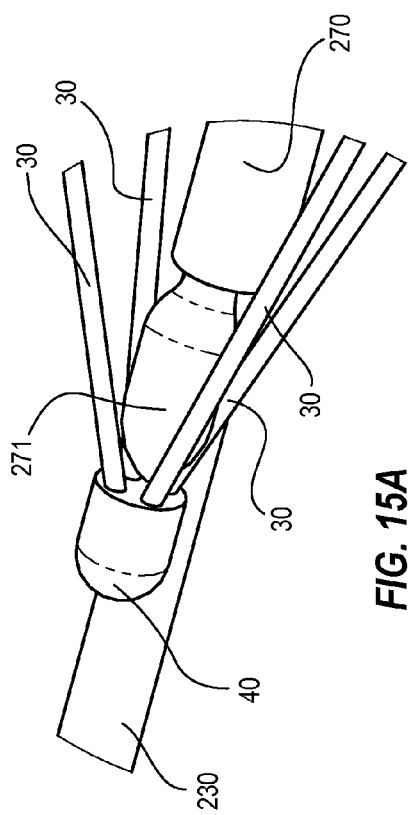
FIG. 15
FIG. 15A

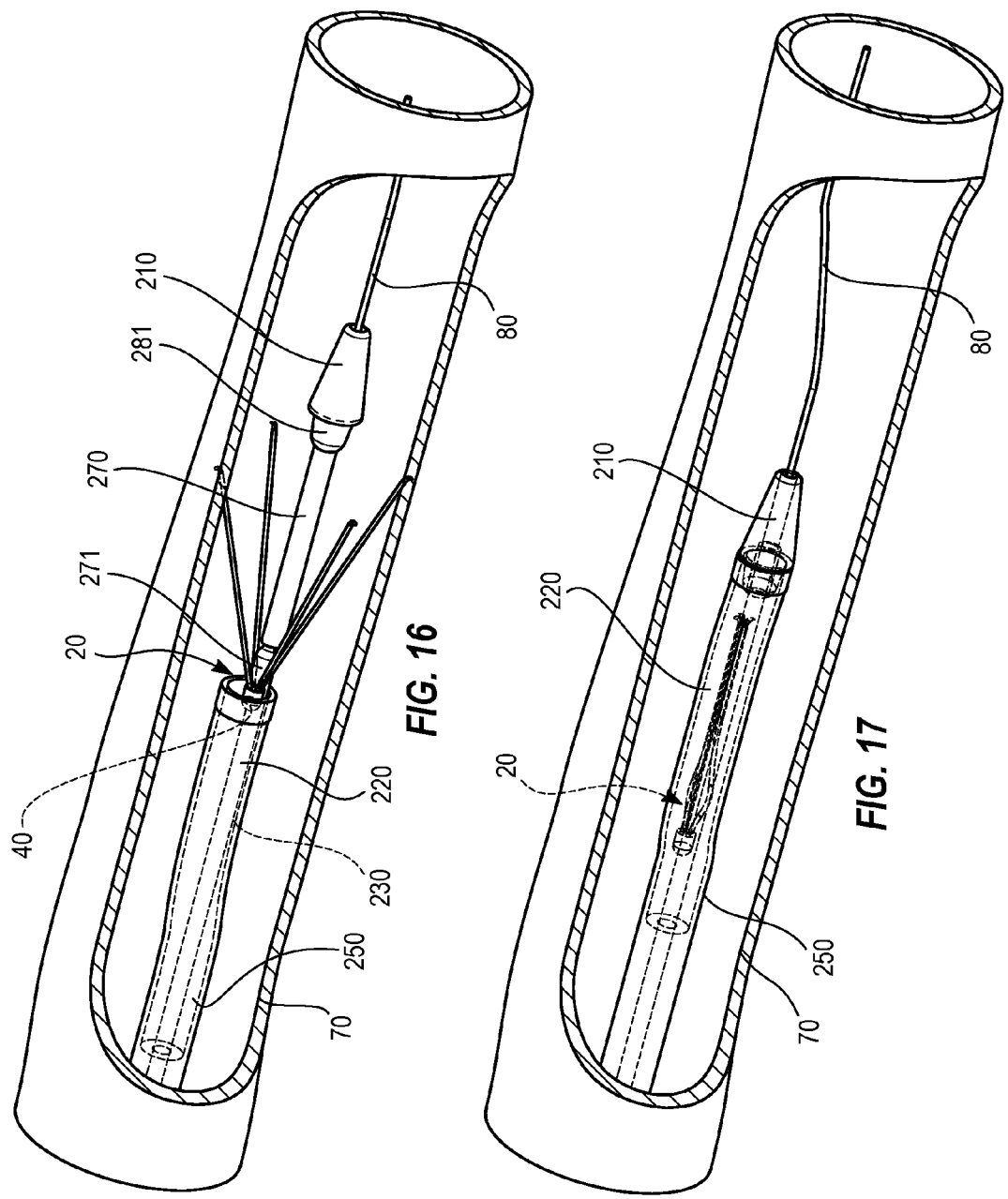

BLOOD FILTER RETRIEVAL DEVICES AND METHODS

CROSS-REFERENCE TO RELATED APPLICATIONS

This application is a national stage application under 35 U.S.C. §371 of International Application No. PCT/US2010/023245, titled BLOOD FILTER RETRIEVAL DEVICES AND METHODS, filed Feb. 4, 2010, which claims priority to U.S. Provisional Patent Application No. 61/150,002, titled BLOOD FILTER RETRIEVAL DEVICES AND RELATED METHODS, filed Feb. 4, 2009, the entire contents of each of which is hereby incorporated by reference herein.

TECHNICAL FIELD

The present disclosure relates to the removal of blood filters from blood vessels. More specifically, the present disclosure is directed to devices and methods for retrieving blood filter devices from within blood vessels.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 2 is a broken perspective view of an embodiment of a filter retrieval device shown in a closed orientation;

FIG. 3 is a broken perspective view of the filter retrieval device of FIG. 2 shown in an open orientation;

FIG. 3A is an enlarged perspective view of a portion of the filter retrieval device of FIG. 2 taken along the view line 3A in FIG. 3;

FIG. 13 is a perspective view of the filter retrieval device of FIG. 10 shown in a closed orientation and having been advanced over a guide wire within a blood vessel to a position near an intravascular filter;

FIG. 14 is a perspective view of the filter retrieval device of FIG. 10, similar to the view of FIG. 13, but showing the filter retrieval device in an open orientation with a catch portion thereof engaging a leg of the intravascular filter;

FIG. 15 is a perspective view of the filter retrieval device of FIG. 10, similar to the view of FIG. 14, but showing the catch portion advanced along the leg of the intravascular filter toward a body of the filter;

FIG. 15A is an enlarged perspective view of the catch portion and the body of the intravascular filter taken along the view line 15A in FIG. 15;

FIG. 16 is a perspective view of the filter retrieval device of FIG. 10, similar to the view of FIG. 15, but showing the intravascular filter being moved within a sheath of the filter retrieval device; and FIG. 17 is a perspective view of the filter retrieval device of FIG. 10, similar to the view of FIG. 16, but showing the filter retrieval device in the closed orientation with the intravascular filter positioned within a sheath of the filter retrieval device.

Figure 1:
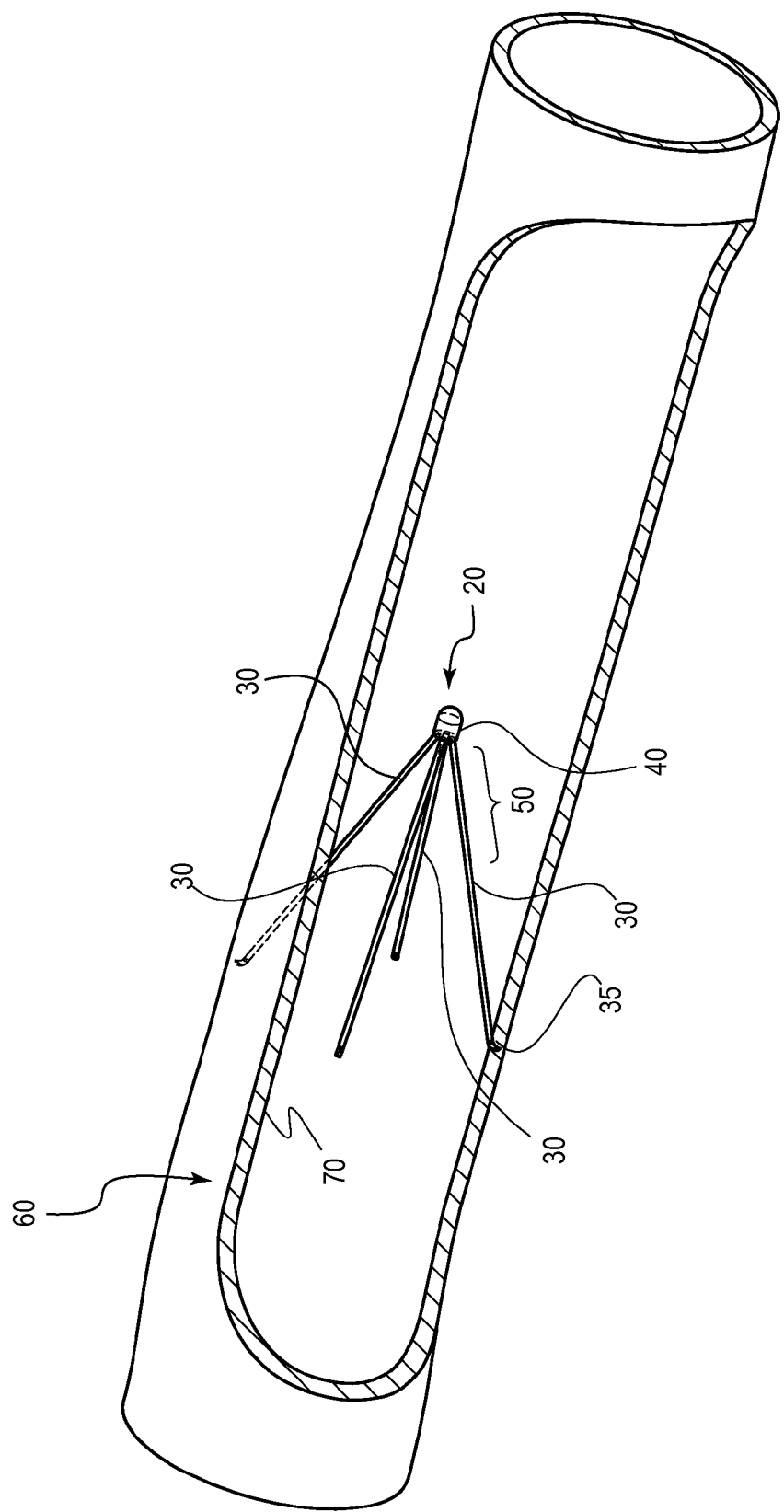
FIG. 1 is a perspective view of an embodiment of an intravascular filter, such as a blood filter.

INDEX OF ELEMENTS IDENTIFIED IN THE DRAWINGS 20 filter
40 body
30 legs
35 wall anchor
50 catch landing
60 blood vessel
70 vessel wall
80 guide wire
100 filter retrieval device
102 core assembly
104 intermediate assembly
106 outer assembly
110 introducer tip
120 sheath
122 core lumen
123 sheath lumen
124 ring
125 sheath edge
130 pass-thru tube
140 core assembly manipulator
141 grip
150 catheter
151 catheter lumen
160 outer assembly manipulator
161 grip
170 catch tube
171 catch
172 catch tube lumen
180 spacer tube
181 tapered portion of spacer tube
182 spacer tube lumen
190 intermediate assembly manipulator
191 grip
200 filter retrieval device
210 introducer tip
220 sheath
230 pass-thru tube 240 core assembly manipulator
250 catheter
260 outer assembly manipulator
270 catch tube
271 catch
280 spacer tube
281 tapered portion

DETAILED DESCRIPTION

Intravenous filters are commonly used to trap blood clots (emboli) carried in the vasculature. Such emboli may cause serious health risks including embolization and thrombosis, and may ultimately lead to death. For example, such emboli, if left unrestrained, may travel to the lungs through the vasculature, resulting in pulmonary embolism. A filter may be positioned in a blood vessel, such as the vena cava, in order to capture emboli and prevent their harmful effects. Such filters often include a body portion from which a plurality of legs extend. The legs can comprise resilient members that are expanded within a vessel in order to center the body within the vessel.

It can be desirable to remove a filter from the vessel, such as after a period of about two to four weeks and/or upon successful elimination of a health risk. In some instances, it can be difficult to remove a filter from a vessel using conventional techniques, such as when the filter is not ideally positioned. For example, in some instances, a filter may shift, rotate, or tilt within the vessel or, stated otherwise, may not be centered within the vessel.

Certain embodiments of filter retrieval devices disclosed herein can be well-suited for removing intravascular filters from within vessels. Embodiments of the devices can be configured to readily remove filters that may not be centered within the vessels or otherwise may be difficult to remove using conventional techniques. As discussed hereafter, some embodiments of a filter retrieval device can include separate components that can translate and rotate relative to each other so as to achieve a desired alignment of the various components in the vicinity of an intravascularly positioned filter. The components, while moveable relative to each other, can be flexible along their length so as to enable the filter retrieval device to be introduced into a lumen of a vessel and follow a contour thereof as the filter retrieval device is advanced to the position at which the intravascular filter is located. The filter retrieval device can include a catch that is enclosed within the device during insertion and subsequently exposed when it is inside the vessel. The catch can be positioned so as to engage or interact with a feature on the filter and/or to move the filter into another portion of the filter retrieval device, such as into a sheath. In some embodiments, the filter retrieval device comprises externally positioned actuators or manipulators that may be used to move one or more of the catch and the sheath relative to each other to achieve a desired alignment of the catch and the sheath. These and other features of embodiments of filter retrieval devices, as well as the advantages thereof, will be apparent from the disclosure herein.

FIG. 1 depicts an illustrative embodiment of an intravascular filter that can be positioned within a blood vessel for any suitable purpose. For example, the filter can be used to capture emboli, as discussed above. FIGS. 2-9 and 10-17 depict first and second embodiments of filter retrieval devices, respectively, that can be used to remove an intravascular filter from a vessel. For example, the filter retrieval devices can be configured to remove the intravascular filter depicted in FIG. 1 from a vessel. Other embodiments of filters and filter retrieval devices can vary from those depicted in the drawings, as discussed further herein.

With reference to FIG. 1, a filter 20 includes a tip or body 40 and legs 30 that extend from the body 40. The legs 30 can extend generally in a single direction, such as in an upstream direction, when the filter has been positioned within a blood vessel 60. The legs 30 may be biased to expand from a radially constrained orientation, in which they may be substantially parallel to each other, to a deployed or expanded position, such as that shown in FIG. 1. For example, the legs 30 may be maintained in the constrained orientation when they are within a delivery device (not shown), and the legs 30 may be permitted to expand when the filter 20 is released from the delivery device or otherwise positioned thereby within the blood vessel 60. The expanded legs 30 can engage a wall 70 of the blood vessel 60 via wall anchors 35, which may be positioned at an end of the legs 30 that is opposite the body 40. As shown, the filter 20 can be maintained in a fixed position relative to the vessel wall 70 via the wall anchors 35. In some embodiments, the wall anchors 35 can include hooks or barbs, which may partially penetrate or otherwise grasp or engage the vessel wall 70 so as to prevent the filter 20 from migrating downstream or tilting after deployment. In other embodiments, the filter 20 can have different configurations from that shown in FIG. 1, such as more or fewer legs 30 and/or legs 30 that are not substantially linear. For example, in various embodiments, the legs 30 can be curved, meshed, or serpentine.

In some embodiments, one or more of the legs 30 can include a landing region or catch landing 50. The catch landing 50 can extend at least a portion of the distance between opposing ends of the legs 30. In the illustrated embodiment, the catch landings 50 are generally positioned at the end of the legs 30 nearest the body 40. As described further below, a catch landing 50 can assist in capture or retrieval of the filter 20, and may serve as a target and/or a guide for directing a catch portion of a filter retrieval device toward the body 40 of the filter 20. In the illustrated embodiment, each catch landing 50 comprises a straight segment of a leg 30 that leads from a central region of the leg 30 toward the filter body 40. In other embodiments, the catch landing 50 may include a coating, covering, or other surface treatment, or may comprise a different material, that provides a greater coefficient of friction to a portion of the leg 30, as compared with remaining portions of the leg 30.

Figure 4:
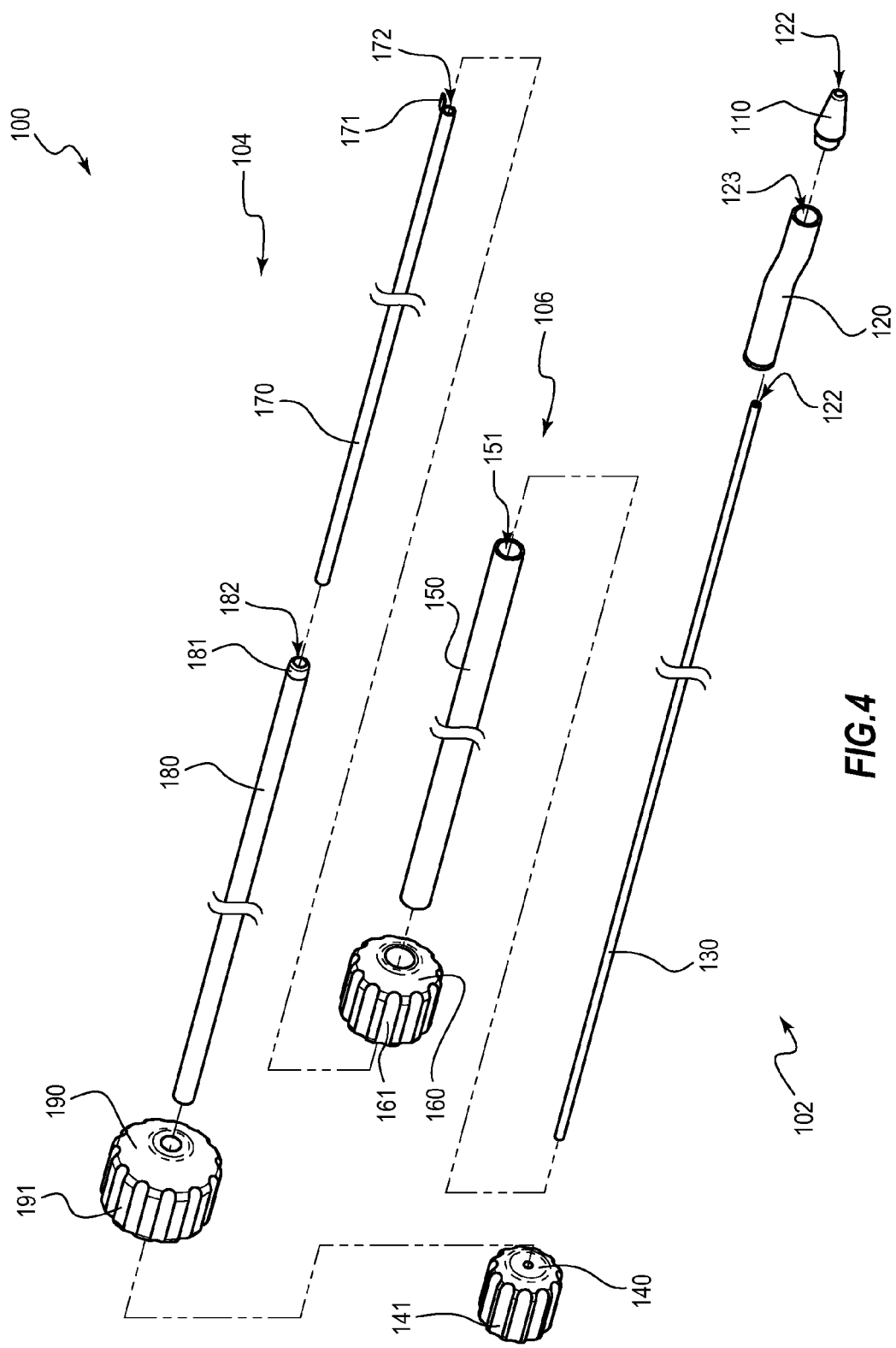
FIG. 4 is a broken, exploded perspective view of the filter retrieval device of FIG. 2.

FIGS. 2-4 illustrate an embodiment of a filter retrieval device 100, which can be used to remove a filter, such as the filter 20, from within a blood vessel. In FIG. 2, the filter retrieval device 100 is shown in a closed orientation, which can be suitable for introduction of the filter retrieval device 100 into a vessel or removal of the device 100 therefrom; in FIG. 3, the filter retrieval device 100 is shown in an open orientation, which can be suitable for gathering the filter 20 into the device 100; and in FIG. 4, the filter retrieval device 100 is shown in a pre-assembled (or disassembled) state to facilitate identification of its various components and discussion of their interrelations.

As shown in FIG. 4, the filter retrieval device 100 can include three separate assemblies that are configured to move relative to one another. Specifically, the filter retrieval device 100 can include a core assembly 102, a intermediate assembly 104, and an outer assembly 106, which are shown, respectively, along three separate levels. As further discussed below, at least a portion of the core assembly 102 can be positioned within the intermediate assembly 104, and at least a portion of the intermediate assembly 104 can be positioned within the outer assembly 106.

In the illustrated embodiment, the core assembly 102 includes an introducer tip 110, a sheath 120, a pass-thru tube 130, and a core assembly actuator or manipulator 140. The tip 110 is at a distal end of the core assembly 102 and the core assembly manipulator 140 is at a proximal end thereof. The tip 110 can be fixedly attached to a distal end of the sheath 120 and/or a distal end of the pass-thru tube 130 in any suitable manner, and the core assembly manipulator 140 can be fixedly attached to a proximal end of the pass-thru tube 130 in any suitable manner. Accordingly, the core assembly manipulator 140, the pass-thru tube 130, the tip 110, and the sheath 120 can be fixed relative to each other such that longitudinal and/or rotational movement of the core assembly manipulator 140 effects like longitudinal and/or rotational movement of the remaining components of the core assembly 102. As further discussed below, a proximal end of the sheath 120 can be free to move transversely relative to the pass-thru tube 130.

As shown in FIG. 2, the introducer tip 110 can be at a distal end of the assembled filter retrieval device 100. The introducer tip 110 can be tapered such that it decreases in size in the distal direction. The introducer tip 110 thus can facilitate insertion of the filter retrieval device 100 into the lumen of a vessel. The introducer tip 110 can be flexible so as to readily deform to follow a guide wire 80 (see FIG. 5) and/or a lumen the blood vessel, and it can be substantially atraumatic to an inner surface of the vessel. For example, in various embodiments, the introducer tip 110 can comprise a material such as polyvinylchloride, thermoplastic elastomer, or silicone rubber. The introducer tip 110 can define at least a portion of a core lumen 122 of the filter retrieval device 100 through which a guide wire 80 may pass. Accordingly, in some embodiments, the introducer tip 110 can be inserted into a blood vessel 60 over the guide wire 80.

In certain embodiments, at least a portion of the introducer tip 110 is radio opaque. For example, in various embodiments, the introducer tip 110 can comprise one or more radio opaque materials or agents (e.g., barium sulfate, bismuth trioxide, titanium dioxide, or the like). In other or further embodiments, the introducer tip 110 can be coated with a lubricious coating, such as a hydrophilic polymer, silicone oil, or other suitable lubricious material. The coating can facilitate a smooth passage of the introducer tip 110 through skin tissue and through the vessel wall 70.

An outermost perimeter of the introducer tip 110 can be the same or approximately the same as an outer perimeter of the distal end of the sheath 120. Such an arrangement can provide a smooth transition from an outer surface of the introducer tip 110 to an outer surface of the sheath 120, which can facilitate insertion of the filter retrieval device 100 into a vessel 60.

With continued reference to FIGS. 2-4, the sheath 120 can be substantially tubular, and may define a lumen 123 into which the pass-thru tube 130 can be received. As shown in FIG. 4, in the illustrated embodiment, the sheath 120 is shaped substantially as a cylinder that has a first portion transversely offset relative to another portion thereof. The sheath 120 can comprise a resiliently deformable material, such as, for example, polyethylene, and can be configured to transition automatically from a displaced configuration to a natural or resting configuration. The configuration of the sheath 120 shown in FIG. 4 represents the natural or resting configuration of the illustrated sheath 120 such that the sheath 120 is biased toward the depicted configuration. As can be seen in FIG. 3, when the filter retrieval device 100 is in the open orientation, a proximal portion of the sheath 120 can be free to move to this natural configuration. This can result in the proximal portion of the sheath 120 being positioned non-concentrically relative to the pass-thru tube 130, since a distal end of the sheath 120 is fixed in a concentric arrangement relative to the pass-thru tube 130. Stated otherwise, the pass-thru tube 130 can define a longitudinal axis of the filter retrieval device 100, and the proximal end of the sheath 120 can be biased toward a position that is eccentric relative to the longitudinal axis.

Other configurations are possible for providing a bias to the sheath 120. For example, the sheath 120 may naturally define a right cylinder, but the sheath 120 may be fitted with a spring or other biasing element that biases a portion of the sheath 120 away from the longitudinal axis of the filter retrieval device 100. As discussed further below, in some embodiments, an eccentrically biased end of the sheath 120 can facilitate capture of a filter 20 within the sheath 120.

As shown in FIG. 2, the sheath 120 can be flexible in at least a transverse direction relative to the longitudinal axis of the filter retrieval device 100. When the filter retrieval device 100 is in the closed orientation, the proximal end of the sheath 120 can be in a displaced orientation in which it is concentric with the pass-thru tube 130. Manners in which the proximal end can be so displaced into the concentric arrangement when the device 100 is transitioned from the open orientation to the closed orientation are discussed below.

As can be seen in FIG. 2, in some embodiments, the sheath 120 can be transversely bowed relative to the longitudinal axis of the filter retrieval device 100 when the filter retrieval device 100 is in the closed orientation. In some embodiments, the transverse bowing of the sheath 120 is only slight such that it has little effect on insertion of the filter retrieval device 100 within a vessel or removal of the filter retrieval device 100 from the vessel. Accordingly, in some embodiments, at least a portion of the sheath 120 can be non-concentric with the pass-thru tube 130 when the filter retrieval device 100 is in the closed orientation.

In some embodiments, at least a portion of the sheath 120 can be radio opaque, which can aid in orienting the sheath 120 relative to a filter 20 that is within the vasculature of a patient. For example, in the illustrated embodiment, the sheath 120 comprises a ring 124 that comprises one or more radio opaque materials or agents (e.g., barium sulfate, bismuth trioxide, titanium dioxide, or the like).

As shown in FIG. 4, the pass-thru tube 130 can define at least a portion of the core lumen 122 of the filter retrieval device 100 through which a guide wire 80 may pass. The pass-thru tube 130 can be sufficiently flexible to follow a contour of a guide wire 80 within a lumen of a blood vessel (e.g., the pass-thru tube 130 may be transversely flexible), yet can be sufficiently rigid or stiff to be advanced over the guide wire 80 and/or rotated relative thereto (e.g., the pass-thru tube 130 can be longitudinally rigid or have a relatively high columnar strength and/or can be torsion-resistant). Other tubular components of the filter retrieval device 100 can have the same or similar properties.

The core assembly manipulator 140 can extend radially outwardly relative to an outer diameter of the pass-thru tube 130. The manipulator 140 can comprise any suitable shape or configuration. In the illustrated embodiment, the manipulator 140 defines a substantially cylindrical outer surface that includes a plurality of grips 141. The grips 141 comprises a series of longitudinally directed protrusions and valleys that can facilitate grasping and rotating the manipulator 140 between fingers of a practitioner. Other arrangements for the manipulator 140 are possible. In the illustrated embodiment, the manipulator 140 is attached to a distal end of the pass-thru tube 130. In other embodiments, a proximal portion of the pass-thru tube 130 can extend through the manipulator 140.

With reference again to FIG. 4, in the illustrated embodiment, the outer assembly 106 includes a catheter 150 and an outer assembly actuator or manipulator 160 that is fixedly attached to a proximal end of the catheter 150 in any suitable manner. Accordingly, longitudinal and/or rotational movement of the outer assembly manipulator 160 effects like longitudinal and/or rotational movement of the catheter 150.

The catheter 150 can comprise any suitable sheath or tubelike structure configured for insertion into the vasculature of a patient, and can define a lumen 151. As shown in FIG. 2, the catheter 150 can encase a substantial portion of the filter retrieval device 100 when the device 100 is in the closed orientation, which can assist in the insertion and removal of the device 100 into and from a vessel, respectively. In the closed orientation, a distal end of the catheter 150 can be approximated to (e.g., can be adjacent to or can abut) a proximal end of the sheath 120. In the illustrated embodiment, an outer diameter of the distal end of the catheter 150 can be the same or approximately the same as an outer perimeter of the proximal end of the sheath 120. Such an arrangement can provide a smooth transition from an outer surface of the catheter 150 to an outer surface of the sheath 120, which likewise can facilitate insertion of the filter retrieval device 100 into a vessel or removal of the device 100 therefrom.

The outer assembly manipulator 160 can extend radially outwardly relative to an outer diameter of the catheter 150. The manipulator 160 can comprise any suitable shape or configuration, and can resemble the manipulator 140 discussed above. For example, the manipulator 160 can include grips 161, and it can be attached at a proximal region of the catheter 150. In the illustrated embodiment, the manipulator 160 is larger than the manipulator 140, although other comparative sizes are possible. Different sizes or other configurations between the manipulators 140, 160 can assist a practitioner in distinguishing them from each other. Any other suitable method for distinguishing the manipulators 140, 160 from each other likewise may be used. In some embodiments, the sizes and configurations of the manipulators 140, 160 may be substantially identical, and the manipulators 140, 160 can be distinguished from each other based on their respective longitudinal positions.

With reference again to FIG. 4, the illustrated embodiment of the intermediate assembly 104 includes a catch tube 170, a blocking tube or spacer tube 180, and an intermediate assembly actuator or manipulator 190. Both the catch tube 170 and the spacer tube 180 can be fixedly attached to the intermediate assembly manipulator 190 at proximal regions thereof in any suitable manner. Accordingly, the intermediate assembly manipulator 190, the spacer tube 180, and the catch tube 170 can be fixed relative to each other such that longitudinal and/or rotational movement of the intermediate assembly manipulator 190 effects like longitudinal and/or rotational movement of the remaining components of the intermediate assembly 104.

The catch tube 170 can include a catch 171 extending therefrom and can define a lumen 172 that extends from a distal end to a proximal end thereof. In the illustrated embodiment, the catch 171 extends radially outwardly from the catch tube 170 and also projects distally beyond a distal end of the catch tube 170. The catch 171 comprises a protrusion that is relatively wide at a proximal end thereof and that narrows to a rounded end at a distal end thereof. As further discussed below, in some embodiments, the catch 171 can be sufficiently wide to contact multiple legs of a filter 20 simultaneously. The rounded end of the catch 171 can be configured to contact a rearward face of the body 40 of a filter 20. In some embodiments, at least a portion of the catch 171 can be radio opaque. For example, in various embodiments, the catch 171 can comprise one or more radio opaque materials or agents. In some embodiments, the catch 171 comprises stainless steel.

The spacer tube 180 can include a lumen 182, which can be sized to receive the catch tube 170. The spacer tube 180 can, in effect, increase an outer diameter of the catch tube 170 so as to fill at least a portion of the space between an inner diameter of the catheter 150 and an outer diameter of the catch tube 170. Such an arrangement can inhibit or prevent blood flow within the lumen 151 of the catheter 150. The spacer tube 180 likewise can maintain a concentric orientation between the catch tube 170 and the catheter 150. In some embodiments, sufficient space is provided between an outer surface of the spacer tube 180 and an inner surface of the catheter 150 to permit relative movement between the spacer tube 180 and the catheter 150. For example, in some embodiments, the spacer tube 180 is able to translate and/or rotate relative to the catheter 150 with little or no frictional engagement, whereas in other embodiments, the spacer tube 180 and the catheter 150 slide past and/or about (or within) one another.

In the illustrated embodiment, the spacer tube 180 is relatively long and extends over a substantial portion of the catch tube 170 (see, e.g., FIG. 3A). In other embodiments, the spacer tube 180 may extend over only a small portion of the catch tube 170. For example, the spacer tube 180 may be positioned at a distal end of the catheter 150, and it may extend only a small distance in each of the distal and proximal directions. In other or further embodiments, the spacer tube 180 may be fixedly attached to an outer surface of the catch tube 170, or the spacer tube 180 can be integral with the catch tube 170. The spacer tube 180 can include a tapered region or tapered portion 181 at a distal end thereof, as discussed further below.

The intermediate assembly manipulator 190 can extend radially outwardly relative to an outer diameter of the catch tube 170. The manipulator 190 can comprise any suitable shape or configuration, and can resemble the manipulators 140, 160. discussed above. For example, the manipulator 190 can include grips 191. In the illustrated embodiment, the manipulator 190 is larger than both of the manipulators 140, 160, although other comparative sizes are possible, as discussed above.

As depicted in FIG. 4 via a broken line, the various components of the core assembly 102, the intermediate assembly 104, and the outer assembly 106 can be assembled into the arrangement shown in FIGS. 2 and 3. As previously mentioned, FIG. 2 illustrates a closed orientation of the filter retrieval device 100 and FIG. 3 illustrates an open orientation thereof.

With reference to FIG. 2, the catch tube 170 and the spacer tube 180 can be fully encased within the catheter 150 and the sheath 120 when the filter retrieval device 100 is in the closed orientation 100. As previously noted, an outer surface of the filter retrieval device 100 thus can be relatively smooth, and can be free or substantially free of discontinuities between adjacent outer components—specifically, between the catheter 150 and the sheath 120 and between the sheath 120 and the introducer tip 110. In the closed orientation, the core assembly manipulator 140 can be in a retracted or proximally extended position relative to the manipulators 160, 190, and a proximal portion of the pass-thru tube 130 can be exposed.

With reference to FIG. 3, the filter retrieval device 100 can be transitioned to the open orientation by advancing the core assembly manipulator 140 toward the intermediate assembly manipulator 190. This causes the pass-thru tube 130 to move distally, which in turn moves both the introducer tip 110 and the sheath 120 distally relative to the catch tube 170. This distal movement of the sheath 120 can expose a distal end of the catch tube 170 and the catch 171 (see also FIG. 3A). In the illustrated embodiment, when the filter retrieval device 100 is in a fully open orientation, the sheath 120 can be longitudinally spaced from the catch tube 170 such that no portion of the catch tube 170 is within the sheath 120.

Any combination of the assembly manipulators 140, 190, 160 can be translated or rotated relative to each other to effect relative movement between the assemblies 102, 104, 106, respectively. Accordingly, if desired, the catheter 150 can be moved (e.g., translated and/or rotated) relative to one or more of the catch tube 170 and the sheath 120, the catch tube 170 can be moved relative to one or more of the catheter 150 and the sheath 120, and the sheath 120 can be moved relative to one or more of the catch tube 170 and the catheter 150.

For example, the manipulators 140, 190 can be rotated relative to each other to adjust a rotational alignment between the catch 171 and a distal opening of the sheath 120. The manipulators 140, 190 likewise can be approximated to each other to advance the catch 171 into the sheath 120. As previously mentioned, a proximal end of the sheath 120 may be biased toward an asymmetrical or eccentric position relative to the pass-thru tube 130 such that a larger entrance into the sheath 120 exists at one side of the pass-thru tube 130 as opposed to an opposite side thereof. As further discussed below, the ability to rotate the catch 171 out of and into alignment with the enlarged entrance and to advance the catch 171 into the sheath 120 at a desired orientation can assist in inserting a filter 20 into the sheath 120.

With reference to FIG. 3A, in some embodiments, a gap between an interior surface of the pass-thru tube 130 and catch tube 170 can be relatively small, which can inhibit or prevent blood flow within the lumen 172 of the catch tube 170. In some embodiments, sufficient space is provided between an outer surface of the pass-thru tube 130 and an inner surface of the catch tube 170 to permit relative movement between the pass-thru tube 130 and the catch tube 170 to be relatively easy. For example, in some embodiments, the pass-thru tube 130 is able to translate and/or rotate relative to the catch tube 170 with little or no frictional engagement, whereas in other embodiments, the pass-thru tube 130 and the catch tube 170 slide past and/or about (or within) one another.

As further discussed below, the catch 171 can cooperate with the pass-thru tube 130 to define a cavity 173 (see also FIGS. 6A and 7) into which at least a portion of a leg 30 of a blood filter 20 can be received. Accordingly, in some embodiments, an inner surface of the catch 171 can be spaced from an outer surface of the tube 130 by a distance that is no less than about 0.5, 0.75, 1.0, 1.25, or 1.5 times, no more than about 0.5, 0.75, 1.0, 1.25, or 1.5 times, or within a range of from about 0.5 to about 1.5 times or from about 0.75 to about 1.25 times a width (e.g., a diameter) of a leg 30 of a filter 20 with which the filter retrieval device 100 is configured to operate.

With continued reference to FIG. 3A, the tapered portion 181 of the spacer tube 180 can assist in positioning a proximal end of the sheath 120 back over spacer tube 180 and into contact with or proximity to a distal end of the catheter 150 as the filter retrieval device 100 is transitioned back to the closed orientation (i.e., the orientation of FIG. 2). Specifically, the proximal end of the sheath 120 can be urged into an increasingly concentric position via the sloped surface of the tapered portion 181 as the core assembly manipulator 140 is retracted to the position shown in FIG. 2.

FIGS. 5-9 illustrate various stages of an illustrative method for retrieving or extracting an intravascularly positioned filter 20 using an embodiment of the filter retrieval device 100. While the following description is directed to retrieval of the filter 20, it is to be understood that the stages can apply to other forms of manipulating a filter 20 in a vessel, such as, for example, deploying the filter 20, repositioning the filter 20, etc.

Figure 5:
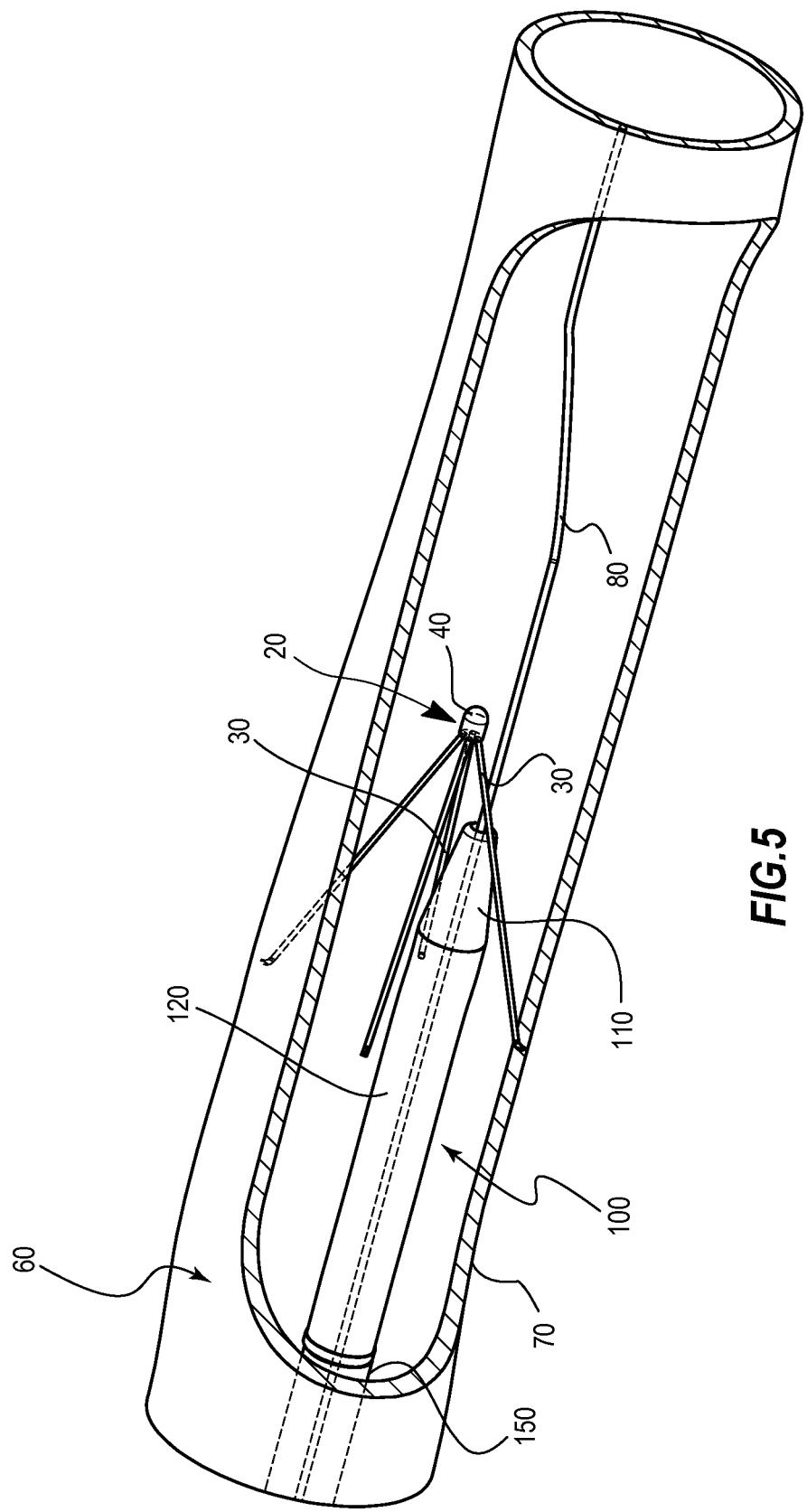
FIG. 5 is a perspective view of the filter retrieval device of FIG. 2 shown in a closed orientation and having been advanced over a guide wire within a blood vessel to a position near a filter.

With reference to FIG. 5, the filter retrieval device 100 can be provided in the closed orientation, and a distal end of the filter retrieval device 100 can be introduced into the vascular system of a patient using any suitable vascular access technique, such as, for example, techniques that are known for devices such as catheters, stents, and balloons. A guide wire 80 can be inserted into a blood vessel 60 and a distal tip thereof can be positioned past the body 40 of the filter 20. A distal end of the filter retrieval device 100 can be advanced over the guide wire 80 and the introducer tip 110 of the device 100 can be directed between a pair of adjacent legs 30 of the filter 20. In the illustrated embodiment, the legs 30 of the filter 20 generally extend away from the body 40 of the filter 20 in an upstream direction, and the filter retrieval device 100 is advanced toward the filter 20 in a downstream direction.

As previously mentioned, various components of the filter retrieval device 100 can be flexible along their lengths to allow the distal end of the filter retrieval device 100 to be manipulated through the vasculature of a patient to the desired location. In particular, each of the pass-thru tube 130, the catch tube 170, the spacer tube 180, and the catheter 150 can be sufficiently flexible to follow a contour of a guide wire 80 within a lumen of the blood vessel 60 (e.g., the components may be transversely flexible), yet can be sufficiently rigid or stiff to be advanced over the guide wire 80, translated relative to each other, and/or rotated relative to each other (e.g., the components can be longitudinally rigid or have a relatively high columnar strength and/or can be torsion-resistant). Any suitable material may be used for the components. For example, in various embodiments, one or more of the components can comprise one or more of polyethylene, polypropylene, polyvinylchloride, and polytetrafluoroethylene. For example, in various embodiments, the pass-thru tube 130 comprises one or more of polyethylene, polypropylene, and polyvinylchloride; the spacer tube 180 comprises one or more of polyethylene, polypropylene, and polyvinylchloride; and the catheter 150 comprises one or more of polyethylene and polytetrafluoroethylene. In some embodiments, the catch tube 170 comprises stainless steel.

Figure 6:
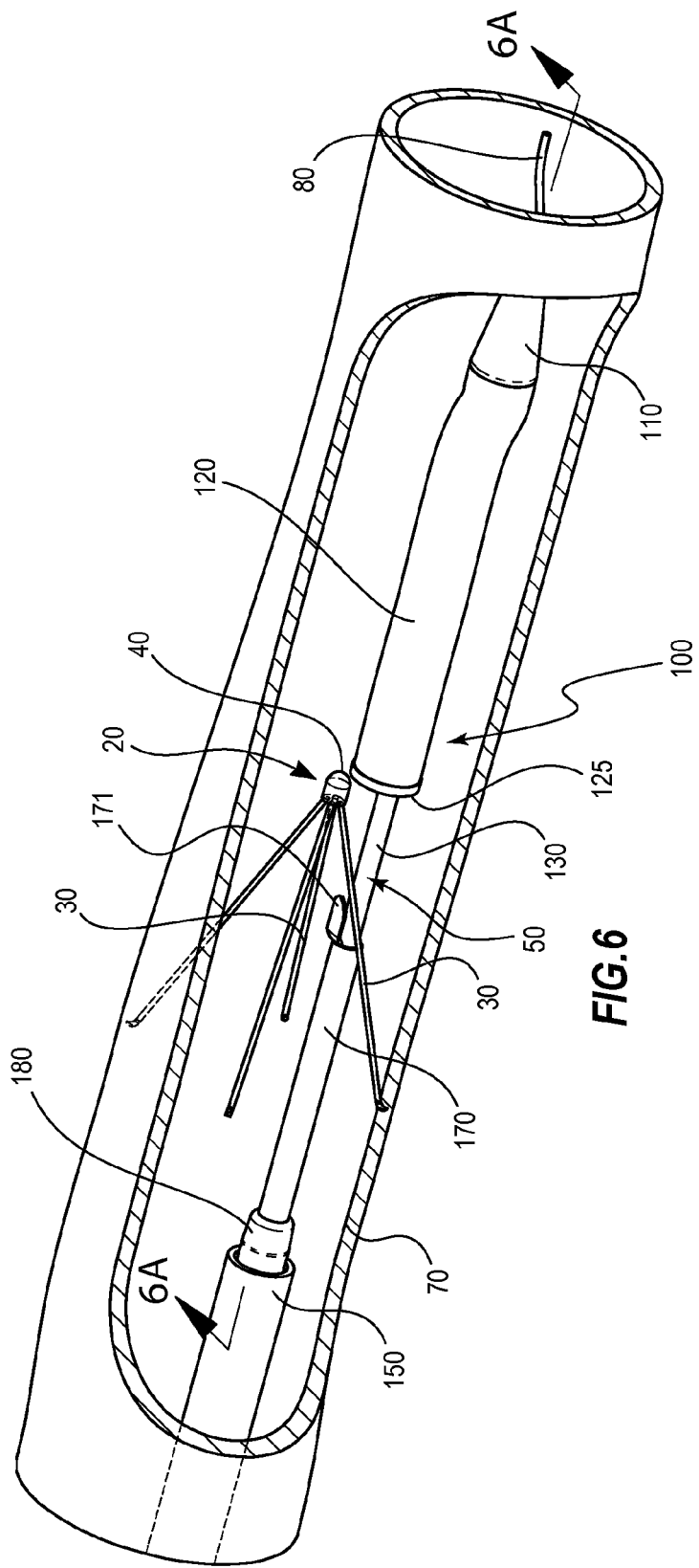
FIG. 6 is a perspective view of the filter retrieval device of FIG. 2, similar to the view of FIG. 5, but with the filter retrieval device shown in an open orientation.

With reference to FIG. 6, the filter retrieval device 100 can be transitioned to the open orientation. Specifically, the sheath 120 can be extended to a position that is beyond (e.g., distal to) the filter body 40. As discussed above with respect to FIGS. 2 and 3, such movement of the sheath 120 can be effected by advancing the core assembly manipulator 140 distally toward the intermediate assembly manipulator 190. As shown in FIG. 6 (as well as FIGS. 6A-8A), the catch 171 can be exposed and can remain at a position that is proximal to the filter body 40 such that at least a portion of the filter body 40 is longitudinally between the sheath 120 and the catch 171.

Figure 6A:
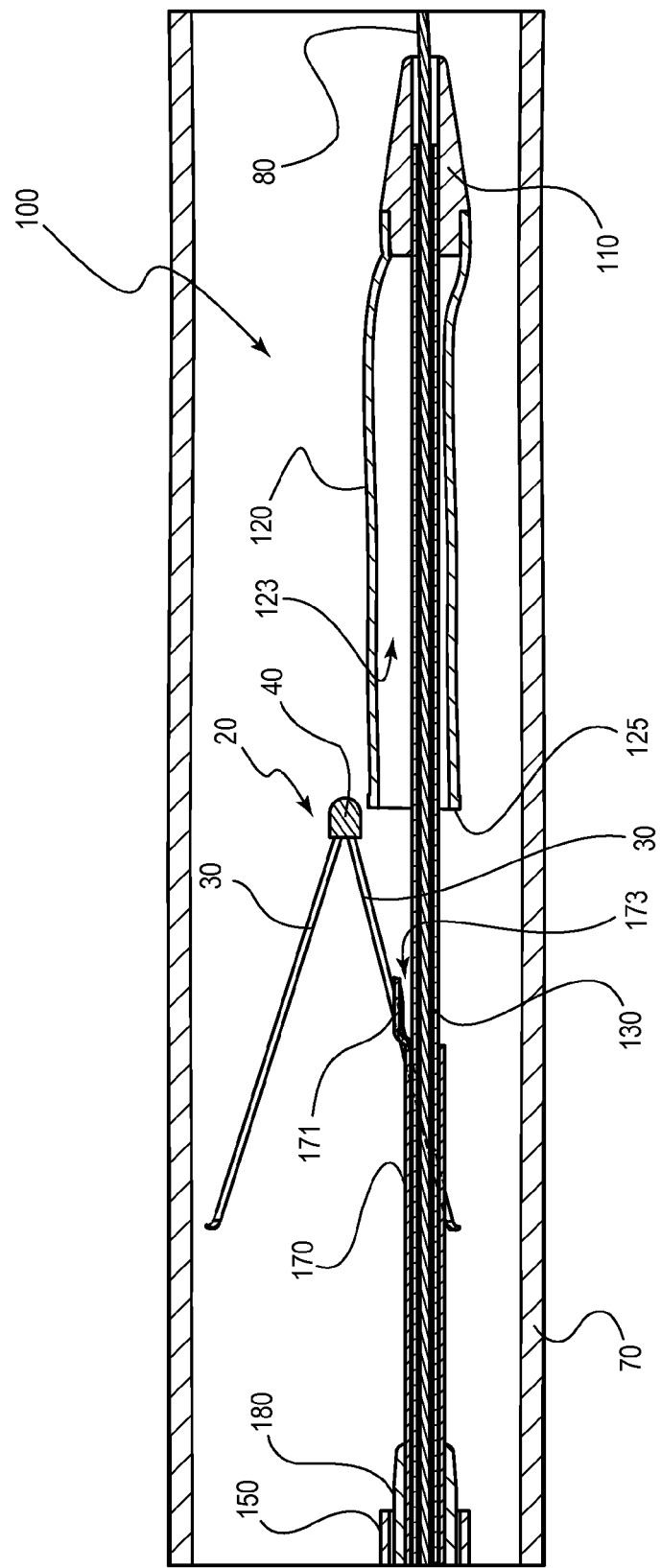
FIG. 6A is a cross-sectional view of the filter retrieval device of FIG. 2 taken along the view line 6A-6A in FIG. 6.

FIG. 6A shows a cross-sectional view of the filter retrieval device 100 in the position illustrated in FIG. 6. As previously discussed, the filter retrieval device 100 has been advanced over the guide wire 80 to the vicinity of the filter 20. As previously mentioned, the filter retrieval device 100 can be free to move along guide wire 80, or stated otherwise, the guide wire 80 can be advanced freely through the filter retrieval device 100. The proximal end of the sheath 120 is shown as having transitioned from the centered configuration (see FIG. 5) to its natural, offset configuration due to the separation of a proximal end of the sheath 120 from the spacer tube 180. The eccentricity or offset of an opening into the lumen 123 of the sheath 120 is clearly visible in the depiction of FIG. 6A. As previously discussed, and as can be seen in FIG. 6A, the enlarged portion of the opening can provide a large target for receiving the filter 20 into the sheath 120.

The catch 171 can be manipulated (e.g. reoriented) longitudinally along and/or rotated around the pass-thru tube 130 in manners such as discussed above so as to be positioned at a catch landing 50 of a leg 30 of the filter 20. Imaging methods such as, for example, angiography, ultrasound, or the like, can be used in positioning the catch 171 at or on a catch landing 50. In some cases, it also can be desirable to position at least a distal end of the body 40 of the filter 20 within the sheath 120 to assist in movement of the catch 171 along a catch landing 50, which can also be assisted by the use of imaging techniques. FIGS. 6 and 6A show the catch 171 being manipulated toward a catch landing 50 of a leg 30 of the filter 20, and also show a proximal edge 125 of the sheath 120 being manipulated to a position over a distal tip of the body 40 of the filter 20.

Figure 7:
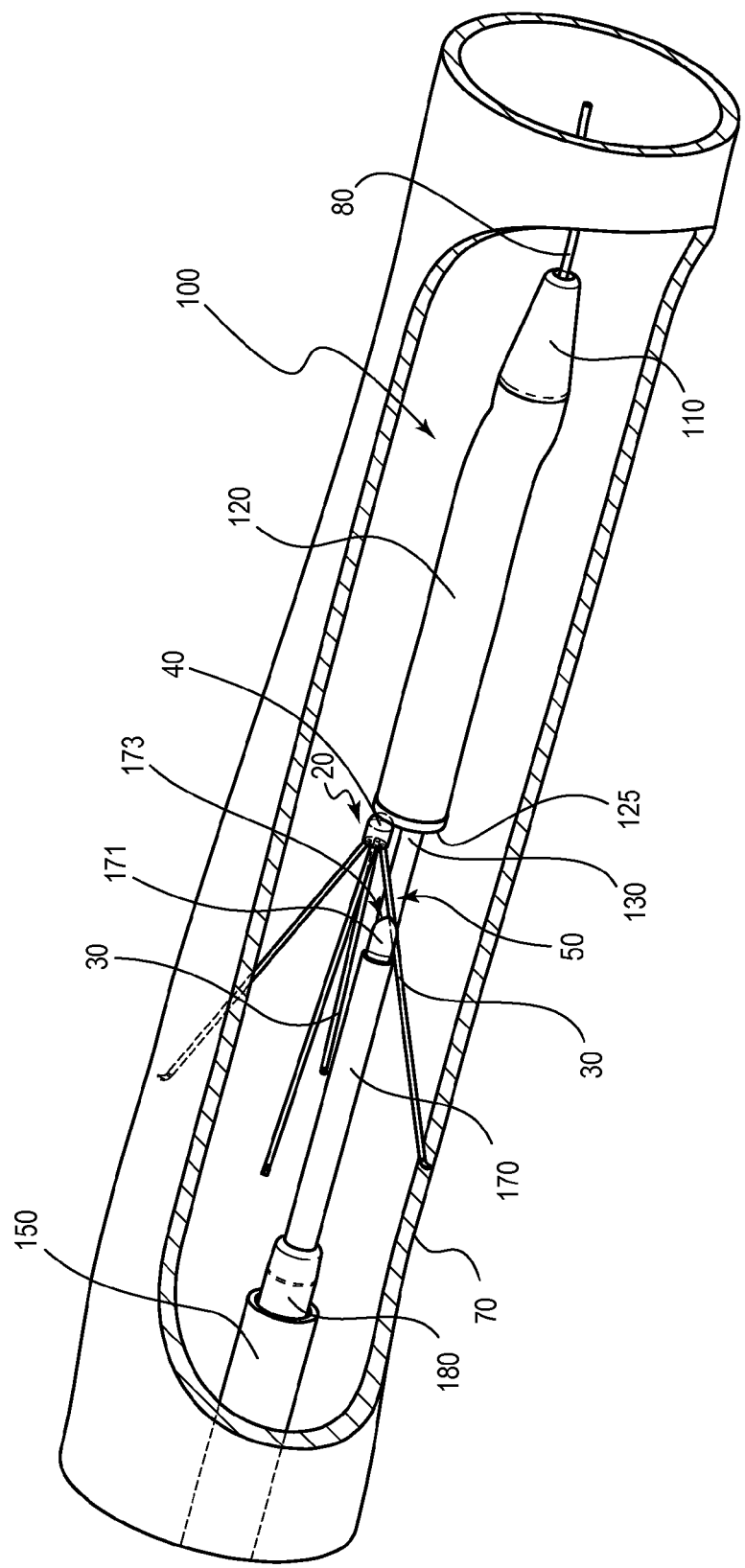
FIG. 7 is a perspective view of the filter retrieval device of FIG. 2, similar to the view of FIG. 6, but showing a catch portion of the device engaging a leg of the intravascular filter.

FIG. 7 illustrates a stage just after the catch 171 has contacted a catch landing 50 and the proximal end 125 of the sheath 120 has been positioned over a distal tip of the body 40. In the illustrated embodiment, the cavity 173 that is defined by the catch 171 and the pass-thru tube 130 is sufficiently large to receive a full diameter of the captured leg 30 of the filter 20 therein. In other embodiments, a height or depth of the cavity 173 may be smaller than a full diameter of the leg 30.

Once the catch 171 engages the landing 50, the catch 171 can be advanced along the catch landing 50 toward the body 40. As the catch 171 is guided along the catch landing 50 (e.g., advanced along or over the catch landing 50), it can ride up between adjacent legs 30 of the filter 20 at a position in which the legs 30 are in close proximity to each other. For example, in some instances, the full filter retrieval device 100 can be advanced distally and/or rotated to advance the catch 171 over the catch landing 50. In other instances, the intermediate assembly manipulator 190 (see FIG. 3) can be twisted and advanced longitudinally relative to one or more of the core assembly manipulator 140 and the outer assembly manipulator 160 to advance the catch 171 toward the filter body 40.

Due to a width of the catch 171 in a direction transverse to a longitudinal axis of the catch tube 170, the catch 171 can simultaneously contact multiple legs 30 as it is advanced closer to the filter body 40, which can yield a wedging or binding effect that tends to secure the filter 20 to the catch 171. The wedging effect also can result in a self-centering of the catch 171 behind filter body 40. Moreover, in some embodiments, a radial thickness of the catch 171 can contribute to the wedging or binding effect. For example, the radial thickness can permit the catch 171 to contact more filter legs 30 as it approaches the filter body 40 and/or can result in greater deformation of the filter legs 30 that it contacts, which can yield a greater binding force between the legs 30 and the catch 171.

Once the catch 171 has been advanced into proximity with the filter body 40 such that the filter legs 30 bind against the catch 171, the filter body 40 can be readily aligned with the enlarged opening of the sheath 120. For example, in some embodiments, the binding force of the legs 30 is sufficient to securely attach the filter 20 to the catch 171 such that rotation of the catch 171 can cause the filter 20 to rotate therewith. Thus, the sheath 120 can be held in place and the catch tube 170 can be rotated relative thereto so as to align the filter body 40 with the enlarged opening. In other or further embodiments, once the catch 171 has been approximated to the filter body 40 so as to produce the binding effect, the catch 171 can then be held steady and the sheath 120 can be rotated so as to align the enlarged opening thereof with the filter body 40. Once the filter body 40 and the enlarged opening of the sheath 120 are aligned, the sheath 120 can be readily drawn over the filter 20, as further discussed below. In some instances, the alignment between the filter body 40 and the enlarged opening of the sheath 120 can be such that the filter body 40 is substantially coaxial with the transversely displaced proximal end of the sheath 120. Alignment and adjustment techniques as just described can be particularly useful in recovering filters 20 that are off-center or tilted within the vessel 60.

In some embodiments, the filter 20 is attached to the vessel wall 70 sufficiently strongly to maintain its position relative to the vessel wall 70 as the catch 171 is advanced toward the body 40. In other or further embodiments, a tip of the body 40 can be held in place by the sheath 120 so as to permit the catch 171 to be advanced toward the body 40.

In some embodiments, a distal edge of the catch 171 may come into contact with a proximal surface of the body 40 once the catch 171 has been approximated thereto. In other embodiments, binding of the legs 30 of the filter 20 can prevent the distal edge of the catch 171 from contacting the proximal surface of the body 40.

Figure 8:
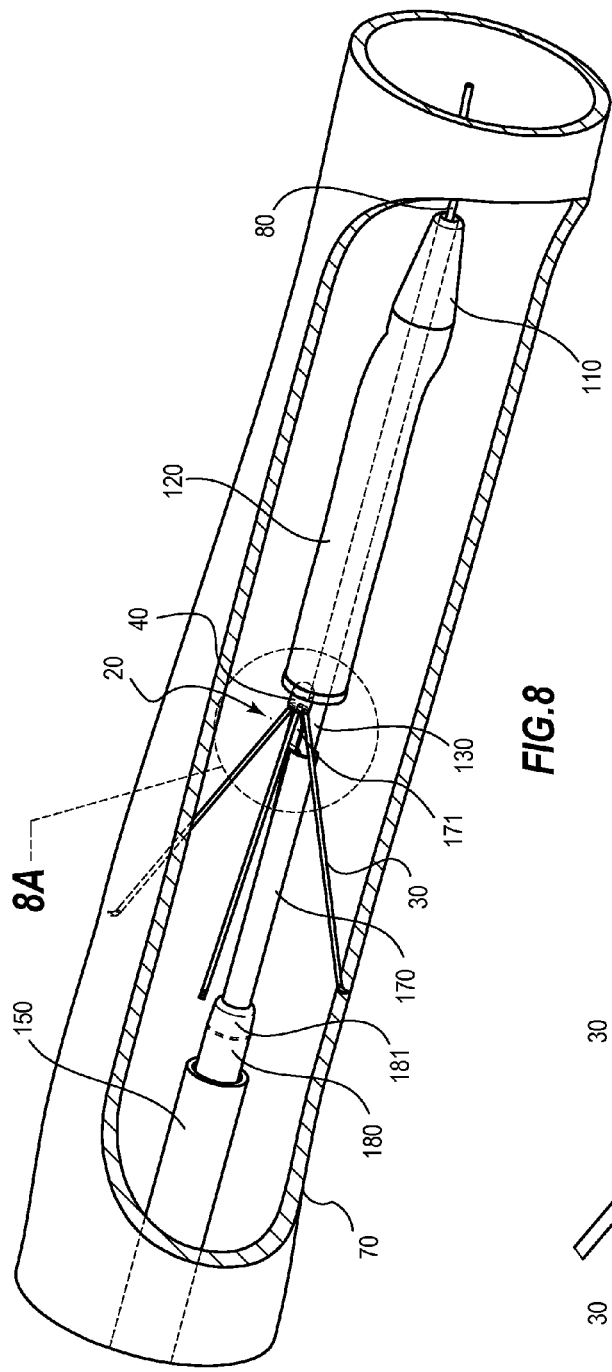
FIG. 8 is a perspective view of the filter retrieval device of FIG. 2, similar to the view of FIG. 7, but showing the catch portion advanced along the leg of the intravascular filter toward a body of the filter.
Figure 8A:
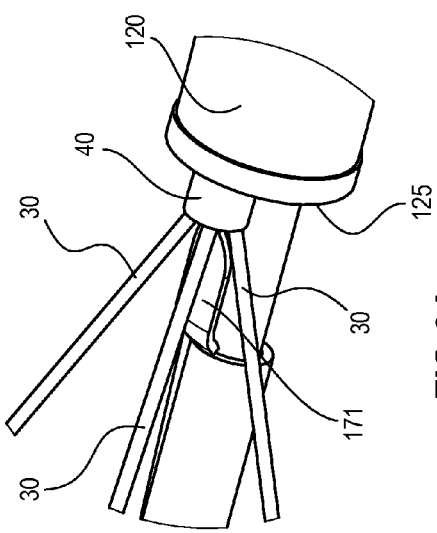
FIG. 8A is an enlarged perspective view of the catch portion and the body of the intravascular filter taken along the view line 8A in FIG. 8.

FIG. 8 illustrates a stage in which the filter 20 has been positioned at the proximal edge 125 of sheath 120 and aligned with the enlarged opening of the sheath 120, and in which the catch 171 is substantially centered relative to a proximal surface of the body 40 of the filter 20. The filter 20 thus is in a convenient orientation for being introduced into the sheath 120. FIG. 8A shows a more detailed view of the catch 171 centered behind the body 40 of the filter 20.

The core assembly manipulator 140 can be drawn in a proximal direction to pull the sheath 120 over the filter 20. As filter body 40 passes into the sheath 120, the proximal edge 125 of the sheath 120 can engage the filter legs 30 and cause them to retract and disengage from the vessel wall 70. In certain embodiments, the sheath 120 can be sufficiently rigid to maintain its longitudinal integrity while the filter 20 is being transitioned into a retracted state and advanced into the lumen 123 of the sheath 120, yet can be sufficiently compliant to deform around the captured filter 20. This property can permit the sheath 120 to maintain a low profile when the filter 20 is captured therein.

Figure 9:
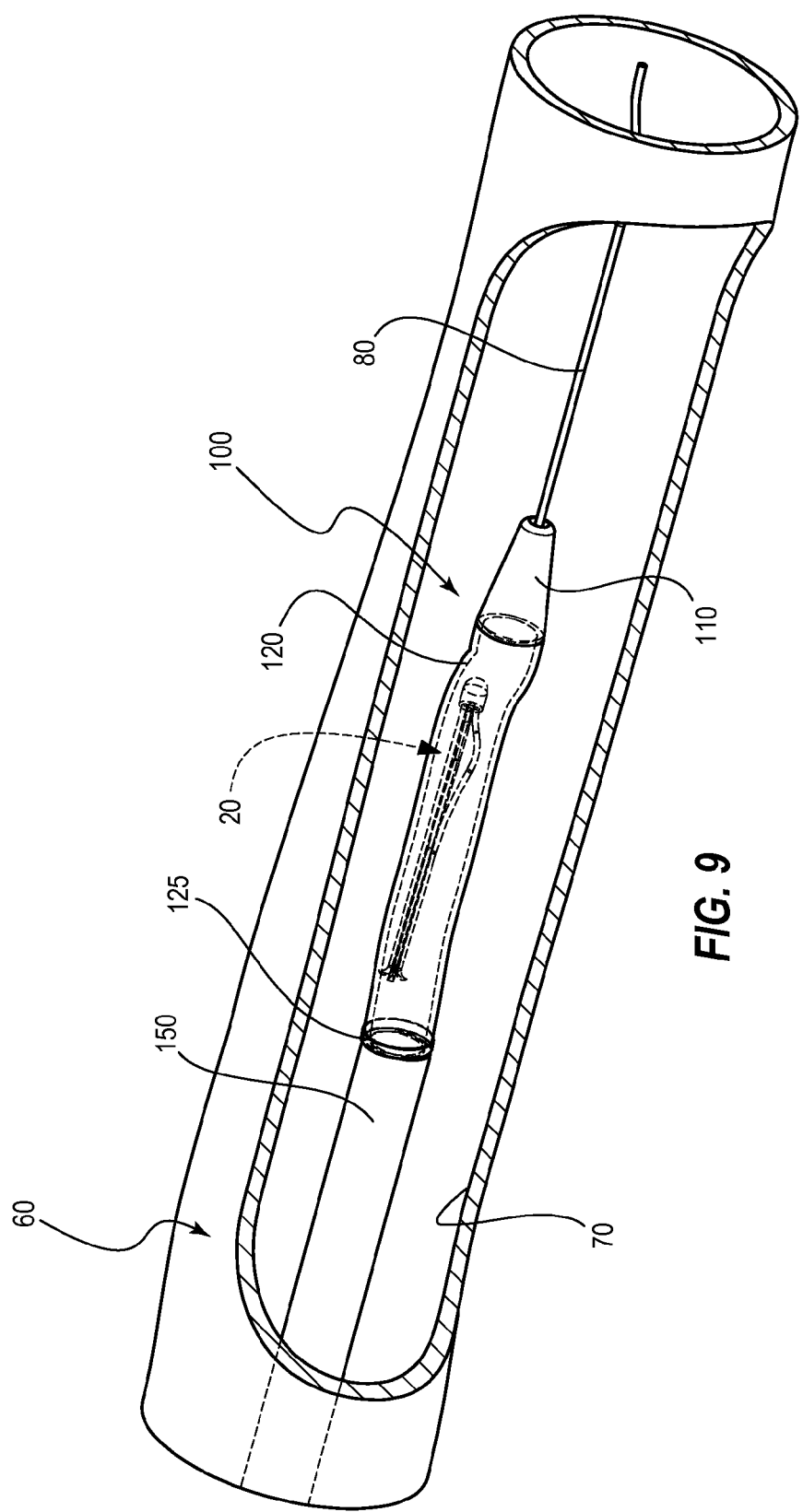
FIG. 9 is a perspective view of the filter retrieval device of FIG. 2, similar to the view of FIG. 8, but showing the filter retrieval device in the closed orientation with the intravascular filter positioned within a sheath of the filter retrieval device.

FIG. 9 illustrates a stage in which the intravascular filter 20 has been fully captured inside of the sheath 120. The proximal sheath edge 125 is positioned over the tapered portion 181 (see FIG. 8) of the spacer tube 180 and is in close proximity to a distal edge of the catheter 150. As previously discussed, the tapered portion 181 can assist in aligning the sheath 120 with the catheter 150 as the sheath 120 is drawn back over the spacer tube 180 as the filter retrieval device 100 is moved to the closed orientation. The catheter 150, the sheath 120, and the introducer tip 110 thus can cooperate to form an inner lumen that is substantially continuous, or which does not include large discontinuities. Such an arrangement also can provide a smooth outer surface along a the inserted length of the filter retrieval device 100, as previously discussed. The filter retrieval device 100, with the filter 20 held therein, can then be removed from the vessel 60.

Other embodiments of the filter retrieval device 100 can have differing features from those described above. For example, in some embodiments, the catch 171 can include a rectangular distal end, and in other or further embodiments, a distal edge may not contact the proximal surface of the body 40 of the filter 20 as the filter is being urged into the sheath 120. In still other or further embodiments, the catch 171 can extend from a more central portion of the catch tube 170, rather than from the distal end thereof.

Figure 10:
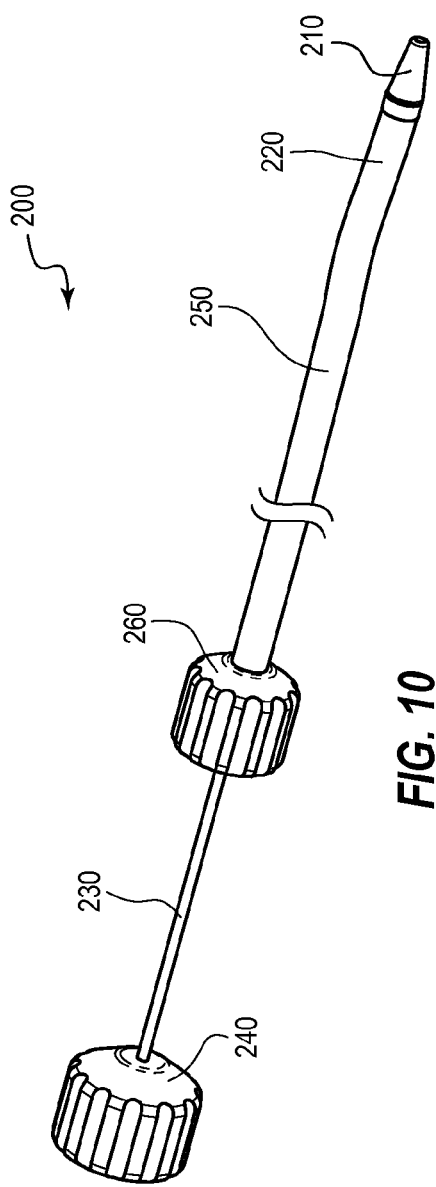
FIG. 10 is a broken perspective view of another embodiment of a filter retrieval device shown in a closed orientation.
Figure 11:
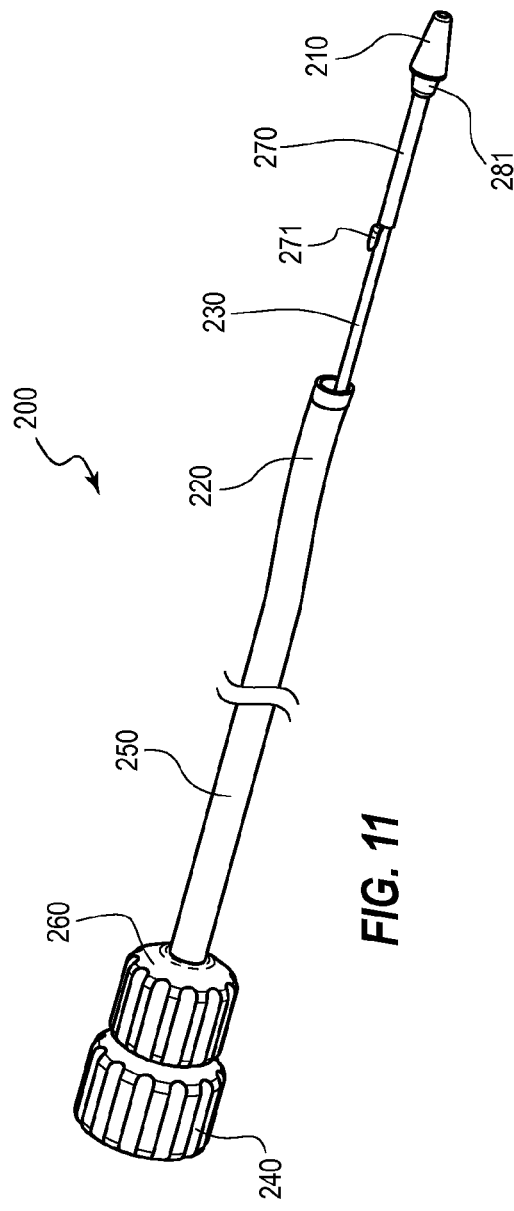
FIG. 11 is a broken perspective view of the filter retrieval device of FIG. 10 shown in an open orientation.
Figure 12:
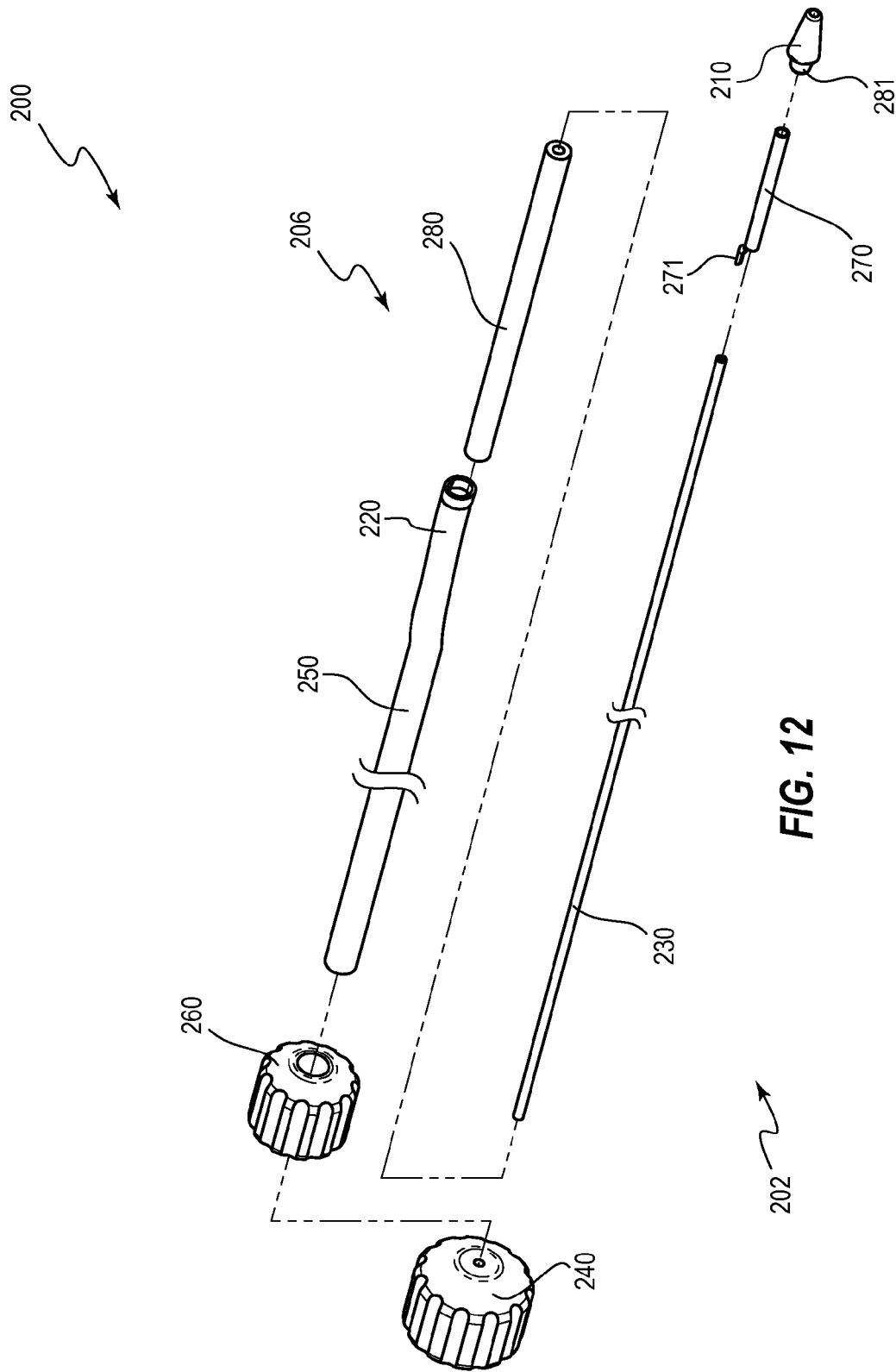
FIG. 12 is an broken, exploded perspective view of the filter retrieval device of FIG. 10.

FIGS. 10-12 illustrate another embodiment of a filter retrieval device 200, which can resemble the filter retrieval device 100 described above in certain respects. Accordingly, like features are designated with like reference numerals, with the leading digits incremented to "2." Relevant disclosure set forth above regarding similarly identified features thus may not be repeated hereafter. Moreover, specific features of the filter retrieval device 200 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the filter retrieval device 200. Any suitable combination of the features and variations of the same described with respect to the filter retrieval device 100 can be employed with the filter retrieval device 200, and vice versa.

In FIG. 10, the filter retrieval device 200 is shown in a closed orientation, which can be suitable for introduction of the filter retrieval device 200 into a vessel or removal of the device 200 therefrom; in FIG. 11, the filter retrieval device 200 is shown in an open orientation, which can be suitable for gathering a filter 20 into the device 200; and in FIG. 12, the filter retrieval device 200 is shown in a pre-assembled (or disassembled) state to facilitate identification of its various components and discussion of their interrelations.

As shown in FIG. 12, the filter retrieval device 200 can include two separate assemblies that are configured to move relative to one another. Specifically, the filter retrieval device 100 can include a core assembly 202 and an outer assembly 206, which are shown on two separate levels. The core assembly 202 can include a core assembly manipulator 240, a pass-thru tube 230, a catch tube 270, and an introducer tip 210. The outer assembly 206 can include an outer assembly manipulator 260, a catheter 250, and a spacer tube 280.

The core assembly manipulator 240 can be fixedly attached to a proximal end of the pass-thru tube 230, and the introducer tip 210 can be fixedly attached to the distal ends of each of the pass-thru tube 230 and the catch tube 270. A catch 271 can extend radially outwardly and in a proximal direction from a proximal end of the catch tube 270.

The outer assembly manipulator 260 can be fixedly attached to a proximal end of the catheter 250. The spacer tube 280 can be shorter than the catheter 250, and a proximal end of the spacer tube 280 likewise can be fixedly attached to a proximal end of the catheter 250. A distal end of the catheter 250, which can extend distally beyond the distal end of the spacer tube 280 when the outer assembly 206 is in an assembled state, can comprise a sheath 220.

As shown in FIGS. 11 and 12, a distal end of the sheath 220 can be biased to an eccentric orientation relative to a longitudinal axis defined by the pass-thru tube 230. Additionally, a distal end of the introducer tip 210 can include a tapered portion 281, which can be configured to centrally align a distal end of the sheath 220 when the filter retrieval device 200 is transitioned to the closed orientation. Interactions between the tapered portion 281 and the sheath 220 can resemble those of the tapered portion 181 and the sheath 120 described above.

When the filter retrieval device 200 is in the closed orientation shown in FIG. 10, an outer surface thereof can be substantially smooth. Additionally, the introducer tip 210 and the catheter 250 can form an inner lumen that is devoid of discontinuities.

The filter retrieval device 200 can be transitioned from the closed orientation shown in FIG. 10 to the open orientation shown in FIG. 11 by approximating at least one of the manipulators 240, 260 to the other. Rotation between the sheath 220 and the catch tube 270 can be achieved by rotating at least one of the manipulators 240, 260 relative to the other. Accordingly, the catch 271 can be manipulated by movement of the outer assembly manipulator 240 along a longitudinal path and/or about a rotational path. Movement of the core assembly manipulator 240 distally and away from the outer assembly manipulator 260 can close the filter retrieval device 200.

FIGS. 13-17 illustrate various stages of an illustrative method for retrieving or extracting an intravascularly positioned filter 20 using an embodiment of the filter retrieval device 200. While the following description is directed to retrieval of the filter 20, it is to be understood that the stages can be used in other forms of manipulating a filter 20 in a vessel, such as, for example, deploying the filter 20, repositioning the filter 20, etc. Moreover, evident similarities between the illustrative stages of a method depicted in FIGS. 5-9, as described above, and the illustrative stage of a method depicted in FIGS. 13-17 may not be discussed hereafter.

As shown in FIG. 13, the distal end of the filter retrieval device 200 can be introduced into the vasculature of the patient using any suitable vascular access technique, such as those known in the art and those yet to be devised. The filter retrieval device 200 can be advanced over the guide wire 80 such that it is directed to the location of the filter 20, which is anchored to the vessel wall 70. The guide wire 80 can be positioned past body 40 of filter 20 and between adjacent legs 30.

The legs 30 of the filter 20 can extend generally in an upstream direction. The filter retrieval device 200 can be advanced within the vessel 60 in an upstream direction. Accordingly, the filter retrieval device 200 can approach the filter 20 from an opposite direction, as compared with the method involving the filter retrieval device 100 depicted in FIGS. 5-9.

As shown in FIG. 14, the introducer tip 210 can be positioned distally beyond the filter body 40 by moving the core assembly manipulator 240 toward the outer assembly manipulator 260 (see also FIGS. 10 and 11). Note that the terms "proximal" and "distal," and variants thereof, are recited from the perspective of an operator using a filter retrieval device 100 or 200. The catch 271 can be exposed and can be manipulated longitudinally or rotationally using outer assembly manipulator 260. The catch 271 can be manipulated to cause the leg 30 to be positioned between the catch 271 and the pass-thru tube 230 on a catch landing 50. Once engaged on the leg 30, the catch 271 can be advanced toward the filter body 40. Note that portions of device 200 may be radio opaque or otherwise perceivable using imaging methods including angiography, ultrasound, or other imaging methods known to those skilled in the art, as discussed above.

FIG. 15 shows the catch 271 having been advanced toward the filter body 40 and guided along the leg 30. The catch 271 can be near or in contact with a distal surface of the filter body 40. The rounded end of the catch 271 may permit binding and/or self-centering in a manner such as described above. As shown in FIG. 15A, the catch 271 may contact two or more, three or more, or all four legs 30 of the filter 20 when approximated to the filter body 40. In other or further embodiments, a tip of the catch 271 may contact the filter body 40 itself.

FIG. 16 shows the eccentric opening of the sheath 220 having been aligned with the filter body 40. The sheath 220 can be advanced over the filter 20, and a distal edge of the sheath 220 can engage the legs 30 and cause the legs 30 to retract. With the legs 30 in a retracted state, the filter 20 can be encased in the sheath 220 by further advancement of a distal edge of the sheath 220 toward the introducer tip 210.

FIG. 17 shows the filter 20 contained within the sheath 220. The filter 20 can be offset relative to a central axis of the filter retrieval device 200.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element.

The invention claimed is:

1. A device for retrieving an intravascular blood filter that has a plurality of retractable legs extending from a body, the device comprising:
   a catch tube comprising a catch extending therefrom that is configured to interact with at least one leg of the blood filter; and
   a sheath that defines a lumen that is configured to receive the blood filter therein when the legs of the filter are in a retracted state, wherein the sheath and the catch tube are rotatable relative to one another and are longitudinally translatable relative to one another such that the device is configured to permit adjustment of a rotational orientation of the catch relative to an opening into the lumen of the sheath so as to assist in introducing the filter into the lumen of the sheath; and
   wherein the device is configured to transition between a closed orientation in which at least a portion of the catch tube is positioned within the sheath and an open orientation in which the catch tube is spaced from the sheath, and
   wherein at least a position of the sheath is non-concentric with the catch tube when the device is in the closed orientation.

2. The device of claim 1, wherein no portion of the catch tube is within the sheath when the device is in the open orientation.

3. The device of claim 1, wherein an end of the sheath is sufficiently rigid to urge the legs of the blood filter into a retracted state as the device is transitioned from the open orientation to the closed orientation.

4. The device of claim 1, wherein the catch is spaced from the sheath and widens in a direction away from the sheath when the device is in an open configuration.

5. The device of claim 1, wherein the catch extends radially outwardly from a body of the catch tube.

6. The device of claim 1, wherein the catch extends either proximally from a proximal end of the catch tube or distally from a distal end of the catch tube.

7. The device of claim 1, further comprising a pass-thru tube that extends through each of the catch tube and the sheath.

8. The device of claim 7, wherein the catch cooperates with the pass-thru tube to define a cavity into which at least a portion of a leg of the blood filter can be received.

9. The device of claim 7, wherein at least a portion of the sheath is non-concentric with the pass-thru tube when the device is in an open orientation in which the filter can be introduced through an open end of the sheath.

10. The device of claim 7, wherein the pass-thru tube defines a lumen through which a guide wire can pass.

11. The device of claim 1, wherein the catch tube defines a lumen such that a guide wire can extend through the device within the catch tube and within the sheath.

12. The device of claim 1, wherein an end of the sheath is configured to move to an eccentric position when the device is transitioned from a closed orientation to an open orientation.

13. The device of claim 1, further comprising a first manipulator attached to and extending radially outwardly from the catch tube at a proximal region thereof and a second manipulator attached to and extending radially outwardly from the sheath at a proximal region thereof, wherein the first and second manipulators are configured to be grasped and manipulated so as to move the catch tube relative to the sheath.

14. The device of claim 1, further comprising a catheter having a distal end that is configured to be approximated to a proximal end of the sheath when the device is in a closed orientation.

15. The device of claim 1, wherein a distal portion of a catheter comprises the sheath.

16. The device of claim 1, wherein the catch is sized to bindingly contact at least two of the legs of the blood filter when it is in close proximity to the body of the filter such that rotation of the catch can effect rotation of the blood filter.

17. A filter retrieval device comprising:
   a pass-thru tube that defines a longitudinal axis;
   a sheath defining a lumen that encompasses the pass-thru tube, wherein at least a portion of the sheath is flexible in at least a direction that is transverse to the longitudinal axis defined by the pass-thru tube, and wherein an end of the sheath is biased toward a position that is eccentric relative to the longitudinal axis; and
   a tapered region configured to move longitudinally relative to the sheath, wherein the tapered region is configured to be spaced from the sheath when the retrieval device is in an open orientation, wherein the tapered region decreases in size toward the sheath when the retrieval device is in the open orientation, and wherein at least a portion of the tapered region is configured to be received within the sheath when the retrieval device is in a closed orientation,
   wherein the end of the sheath is in the eccentric position when the retrieval device is in the open orientation such that a filter can be readily introduced into the lumen of the sheath, and wherein the tapered region is configured to move the end of the sheath to a more centered position relative to the longitudinal axis as the retrieval device is transitioned to the closed orientation.

18. The filter retrieval device of claim 17, further comprising a catheter having a distal end that is approximated to the end of the sheath when the retrieval device is in the closed orientation.

19. The filter retrieval device of claim 17, wherein an outer perimeter of the distal end of the catheter is approximately or exactly the same as an outer perimeter of the end of the sheath such that there is a smooth transition from an outer surface of the catheter to an outer surface of the sheath when the retrieval device is in the closed orientation.

20. The filter retrieval device of claim 17, wherein a distal end of a catheter comprises the sheath.

21. The filter retrieval device of any of claim 17, further comprising a tapered introducer tip at a distal end thereof.

22. The filter retrieval device of claim 21, wherein the sheath is fixedly attached to the introducer tip.

23. The filter retrieval device of claim 21, wherein the tapered region is fixedly attached to the introducer tip.

24. The filter retrieval device of claim 23, wherein the end of the sheath is approximated to a proximal end of the introducer tip when the retrieval device is in the closed orientation.

25. The filter retrieval device of claim 24, wherein an outer perimeter of the distal end of the sheath is approximately or exactly the same as an outer perimeter of the proximal end of the introducer tip such that there is a smooth transition from an outer surface of the sheath to an outer surface of the introducer tip when the retrieval device is in the closed orientation.

26. The filter retrieval device of claim 17, further comprising a catch tube that is configured to move independently of the sheath, wherein the catch tube is configured to assist in moving a filter into the sheath.

27. The filter retrieval device of claim 26, wherein the catch tube is configured to move relative to the sheath in both a longitudinal direction and a rotational direction.

28. The filter retrieval device of claim 26, wherein the catch tube is fixedly attached to the pass-thru tube.

29. The filter retrieval device of claim 17, wherein the tapered region is centered about the longitudinal axis defined by the pass-thru tube.

30. The filter retrieval device of claim 17, wherein the sheath is connected to the pass-thru tube.

31. The filter retrieval device of claim 17, wherein the pass-thru tube defines a lumen therethrough that is sized to receive a guide wire such that the retrieval device can be inserted into a patient over the guide wire.

32. The filter retrieval device of claim 17, wherein an end of the sheath comprises a radio opaque material.

33. A device for retrieving an intravascular blood filter that has a plurality of retractable legs extending from a body, the device comprising:
   a catch tube comprising a catch extending therefrom that is configured to interact with at least one leg of the blood filter;
   a sheath that defines a lumen that is configured to receive the blood filter therein when the legs of the filter are in a retracted state, wherein the sheath and the catch tube are rotatable relative to one another and are longitudinally translatable relative to one another such that the device is configured to permit adjustment of a rotational orientation of the catch relative to an opening into the lumen of the sheath so as to assist in introducing the filter into the lumen of the sheath; and
   a pass-thru tube that extends through each of the catch tube and the sheath; and
   wherein at least a portion of the sheath is non-concentric with the pass-thru tube when the device is in an open orientation in which the filter can be introduced through an open end of the sheath.

34. The device of claim 33, wherein the device is configured to transition between a closed orientation in which at least a portion of the catch tube is positioned within the sheath and an open orientation in which the catch tube is spaced from the sheath.

35. The device of claim 34, wherein at least a portion of the sheath is non-concentric with the catch tube when the device is in the closed orientation.

36. The device of claim 34, wherein no portion of the catch tube is within the sheath when the device is in the open orientation.

37. The device of claim 34, wherein an end of the sheath is sufficiently rigid to urge the legs of the blood filter into a retracted state as the device is transitioned from the open orientation to the closed orientation.

38. The device of claim 33, wherein the catch is spaced from the sheath and widens in a direction away from the sheath when the device is in an open configuration.

39. The device of claim 33, wherein the catch extends radially outwardly from a body of the catch tube.

40. The device of claim 33, wherein the catch extends either proximally from a proximal end of the catch tube or distally from a distal end of the catch tube.

41. The device of claim 33, wherein the catch cooperates with the pass-thru tube to define a cavity into which at least a portion of a leg of the blood filter can be received.

42. The device of claim 33, wherein the pass-thru tube defines a lumen through which a guide wire can pass.

43. The device of claim 33, wherein the catch tube defines a lumen such that a guide wire can extend through the device within the catch tube and within the sheath.

44. The device of claim 33, wherein an end of the sheath is configured to move to an eccentric position when the device is transitioned from a closed orientation to an open orientation.

45. The device of claim 33, further comprising a first manipulator attached to and extending radially outwardly from the catch tube at a proximal region thereof and a second manipulator attached to and extending radially outwardly from the sheath at a proximal region thereof, wherein the first and second manipulators are configured to be grasped and manipulated so as to move the catch tube relative to the sheath.

46. The device of claim 33, further comprising a catheter having a distal end that is configured to be approximated to a proximal end of the sheath when the device is in a closed orientation.

47. The device of claim 33, wherein a distal portion of a catheter comprises the sheath.

48. The device of any of claim 33, wherein the catch is sized to bindingly contact at least two of the legs of the blood filter when it is in close proximity to the body of the filter such that rotation of the catch can effect rotation of the blood filter.

49. A device for retrieving an intravascular blood filter that has a plurality of retractable legs extending from a body, the device comprising:
   a catch tube comprising a catch extending therefrom that is configured to interact with at least one leg of the blood filter; and
   a sheath that defines a lumen that is configured to receive the blood filter therein when the legs of the filter are in a retracted state, wherein the sheath and the catch tube are rotatable relative to one another and are longitudinally translatable relative to one another such that the device is configured to permit adjustment of a rotational orientation of the catch relative to an opening into the lumen of the sheath so as to assist in introducing the filter into the lumen of the sheath; and wherein an end of the sheath is configured to move to an eccentric position when the device is transitioned from a closed orientation to an open orientation.

50. The device of claim 49, wherein the device is configured to transition between a closed orientation in which at least a portion of the catch tube is positioned within the sheath and an open orientation in which the catch tube is spaced from the sheath.

51. The device of claim 50, wherein at least a portion of the sheath is non-concentric with the catch tube when the device is in the closed orientation.

52. The device of claim 50, wherein no portion of the catch tube is within the sheath when the device is in the open orientation.

53. The device of claim 50, wherein an end of the sheath is sufficiently rigid to urge the legs of the blood filter into a retracted state as the device is transitioned from the open orientation to the closed orientation.

54. The device of claim 49, wherein the catch is spaced from the sheath and widens in a direction away from the sheath when the device is in an open configuration.

55. The device of claim 49, wherein the catch extends radially outwardly from a body of the catch tube.

56. The device of claim 49, wherein the catch extends either proximally from a proximal end of the catch tube or distally from a distal end of the catch tube.

57. The device of claim 49, further comprising a pass-thru tube that extends through each of the catch tube and the sheath.

58. The device of claim 57, wherein the catch cooperates with the pass-thru tube to define a cavity into which at least a portion of a leg of the blood filter can be received.

59. The device of claim 57, wherein at least a portion of the sheath is non-concentric with the pass-thru tube when the device is in an open orientation in which the filter can be introduced through an open end of the sheath.

60. The device of claim 57, wherein the pass-thru tube defines a lumen through which a guide wire can pass.

61. The device of claim 49, wherein the catch tube defines a lumen such that a guide wire can extend through the device within the catch tube and within the sheath.

62. The device of claim 49, further comprising a first manipulator attached to and extending radially outwardly from the catch tube at a proximal region thereof and a second manipulator attached to and extending radially outwardly from the sheath at a proximal region thereof, wherein the first and second manipulators are configured to be grasped and manipulated so as to move the catch tube relative to the sheath.

63. The device of claim 49, further comprising a catheter having a distal end that is configured to be approximated to a proximal end of the sheath when the device is in a closed orientation.

64. The device of claim 49, wherein a distal portion of a catheter comprises the sheath.

65. The device of any of claim 49, wherein the catch is sized to bindingly contact at least two of the legs of the blood filter when it is in close proximity to the body of the filter such that rotation of the catch can effect rotation of the blood filter.

* * * * *